US009395450B2

(12) United States Patent
Tezuka

(10) Patent No.: US 9,395,450 B2
(45) Date of Patent: Jul. 19, 2016

(54) RADIATION IMAGING APPARATUS, RADIATION IMAGING SYSTEM, METHOD FOR RADIATION IMAGING, AND STORAGE MEDIUM

(71) Applicant: CANON KABUSHIKI KAISHA, Tokyo (JP)

(72) Inventor: Shimpei Tezuka, Shimotsuke (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 44 days.

(21) Appl. No.: 14/190,169

(22) Filed: Feb. 26, 2014

(65) Prior Publication Data

US 2014/0239188 A1    Aug. 28, 2014

(30) Foreign Application Priority Data

Feb. 28, 2013   (JP) .................................. 2013-040037
Feb. 6, 2014    (JP) .................................. 2014-021705

(51) Int. Cl.
| | |
|---|---|
| *G01T 1/17* | (2006.01) |
| *H04N 5/217* | (2011.01) |
| *H04N 5/361* | (2011.01) |
| *H04N 5/32* | (2006.01) |
| *A61B 6/00* | (2006.01) |

(52) U.S. Cl.
CPC ................ *G01T 1/17* (2013.01); *A61B 6/4233* (2013.01); *A61B 6/586* (2013.01); *H04N 5/2176* (2013.01); *H04N 5/32* (2013.01); *H04N 5/361* (2013.01)

(58) Field of Classification Search
CPC ...... G01T 1/17; A61B 6/1586; A61B 6/4233; H04N 5/32; H04N 5/361; H04N 5/358; H04N 5/2176
See application file for complete search history.

(56) References Cited

U.S. PATENT DOCUMENTS

| | | | | |
|---|---|---|---|---|
| 2005/0047639 | A1* | 3/2005 | Hayashida | ........... H04N 5/3597 382/132 |
| 2005/0128327 | A1* | 6/2005 | Bencuya | ........... H01L 27/14603 348/308 |
| 2010/0327176 | A1* | 12/2010 | Takenaka | ............... H04N 5/335 250/394 |

(Continued)

FOREIGN PATENT DOCUMENTS

| | | |
|---|---|---|
| EP | 2403237 | 1/2012 |
| EP | 2448255 | 5/2012 |

(Continued)

OTHER PUBLICATIONS

EESR issued on Sep. 5, 2014, by the EPO in counterpart EPA 14154974.1 (in English).

*Primary Examiner* — Yara B Green
(74) *Attorney, Agent, or Firm* — Fitzpatrick, Cella, Harper & Scinto

(57) ABSTRACT

A radiation imaging apparatus includes a reset control unit configured to perform reset scanning to sequentially discharge charges accumulated in pixels; an irradiation detection unit configured to detect a start of radiation irradiation based on charges discharged by the reset scanning; an imaging control unit configured to perform control to stop the reset scanning in accordance with detection of the start of irradiation and obtain an image signal by reading out charges accumulated in the pixels; a generation unit configured to generate image data based on the image signal except for an image signal from a pixel on which the reset scanning is performed during the radiation irradiation; and an output unit configured to output the image data to an external apparatus.

27 Claims, 15 Drawing Sheets

(56) References Cited

U.S. PATENT DOCUMENTS

| | | | |
|---|---|---|---|
| 2011/0069209 A1* | 3/2011 | Kanemitsu | H04N 5/3675 348/246 |
| 2012/0201357 A1* | 8/2012 | Watanabe | H04N 5/32 378/114 |
| 2012/0318994 A1 | 12/2012 | Tajima | 250/370.08 |
| 2013/0032696 A1 | 2/2013 | Tajima | 250/208.1 |

FOREIGN PATENT DOCUMENTS

| | | |
|---|---|---|
| JP | 2003-33340 A | 2/2003 |
| JP | 2009-219538 A | 10/2009 |
| JP | 2011-249891 A | 12/2011 |
| JP | 2012-152340 A | 8/2012 |

* cited by examiner

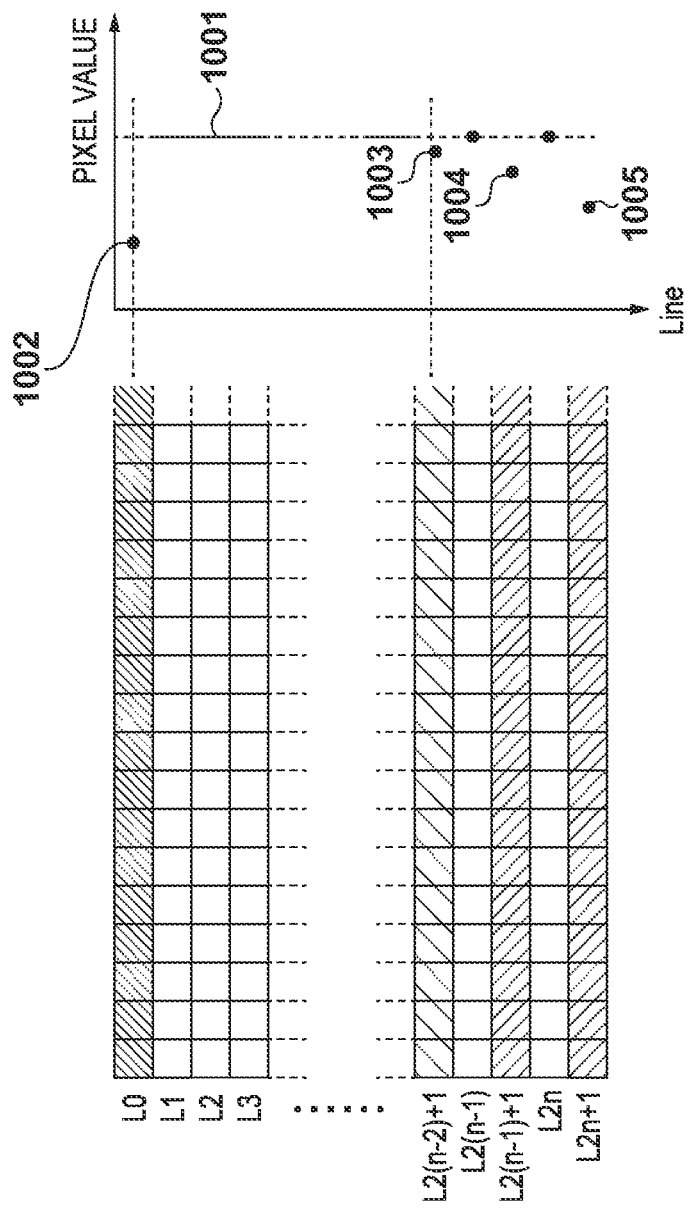

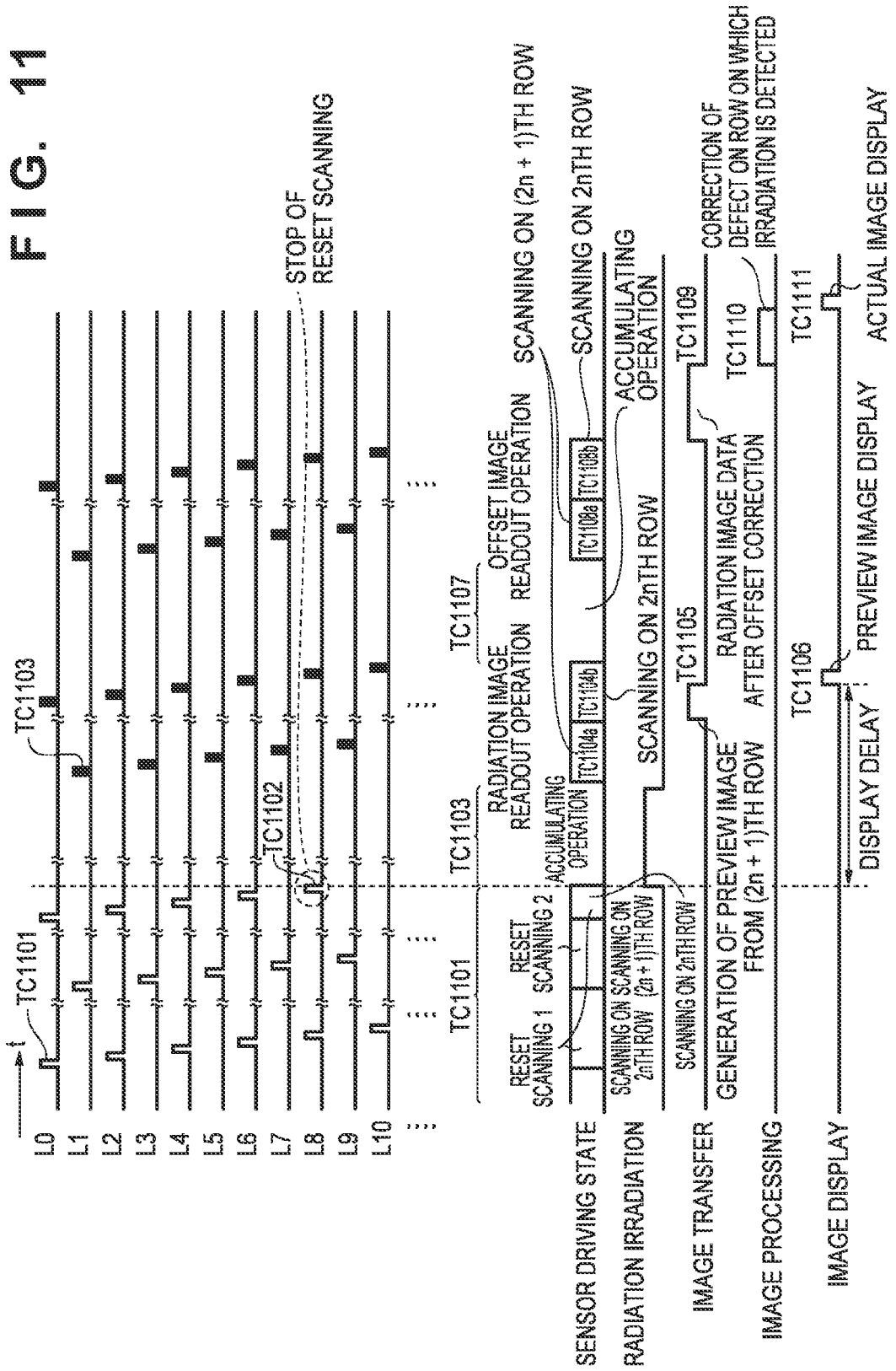

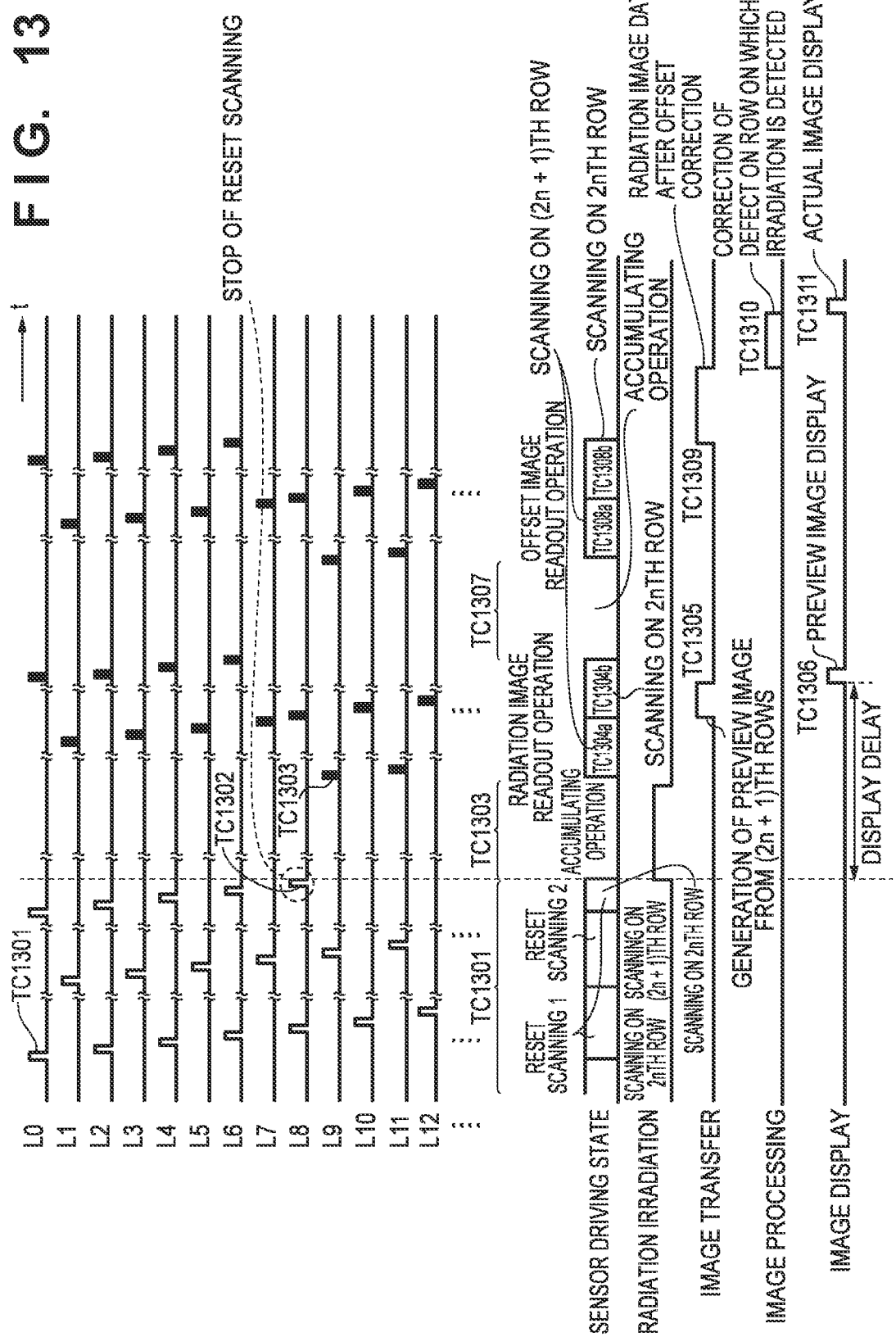

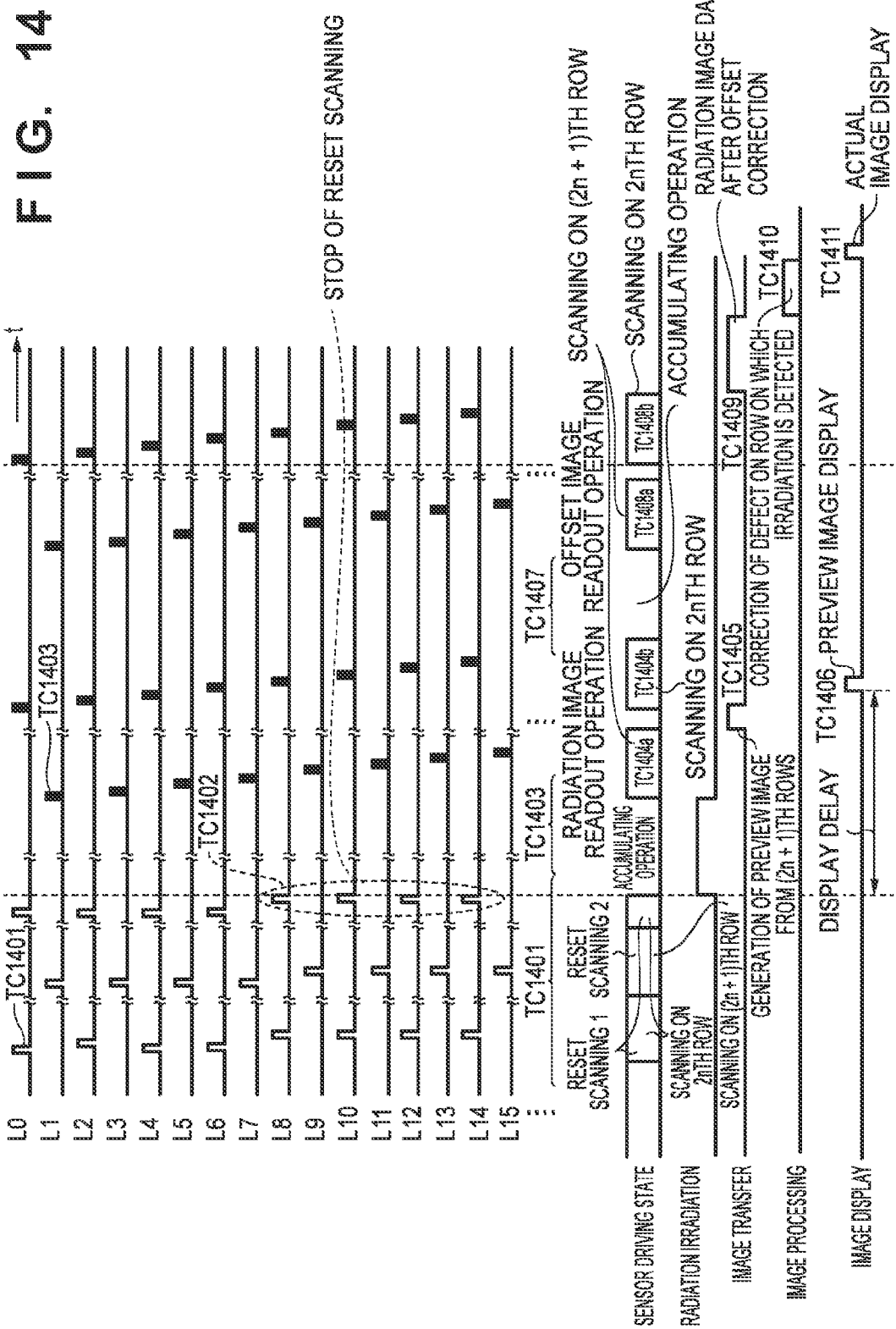

RADIATION IMAGING APPARATUS, RADIATION IMAGING SYSTEM, METHOD FOR RADIATION IMAGING, AND STORAGE MEDIUM

BACKGROUND OF THE INVENTION

1. Field of the Invention

The present invention relates to a radiation imaging apparatus, a radiation imaging system, a method for radiation imaging, and a storage medium.

2. Description of the Related Art

There has been commercially available a radiation imaging system using a radiation generator which irradiates an object with radiation, a radiation imaging apparatus which generates a clear radiation image by performing image processing for the radiation image obtained by digitizing a radiation image as a radiation intensity distribution, and an image processing apparatus. In such a radiation imaging system, the radiation irradiation apparatus irradiates an object with radiation, and the radiation imaging apparatus transfers obtained radiation image data to an image processing apparatus such as a control computer for image processing and saving. The image processing apparatus causes a display apparatus such as a display to display the processed image.

The radiation imaging apparatus uses a sensor array having a two-dimensional array of pixels each including a conversion element which converts radiation into an image signal charge (electrical signals) and a switch element such as a TFT which transfers electrical signals to the outside. Performing matrix driving using switch elements such as TFTs transfers the signal charges converted by the conversion elements to a readout image processing apparatus, thereby forming an image from a readout charge amount.

Each conversion element on the sensor array directly or indirectly generates signals upon being irradiated with radiation. In a sensor designed to indirectly generate signals, the conversion element of each pixel detects the visible light converted from radiation by the phosphor instead of directly detecting the radiation. In either the direct or indirect sensor, each pixel generates and accumulates a certain level of a signal even without any radiation irradiation. This signal is called a dark charge here.

Dark charges have different characteristics in the respective pixels on the array. Superimposing dark charges on image signal charges (electrical signals) originating from radiation irradiation will degrade the image quality in such a manner that offsets are added to the image. To prevent this, it is a general practice to discharge (reset) accumulated dark charges by turning on the switch elements of the respective pixels periodically and/or immediately before radiation irradiation.

When resetting dark charges, if image signals are superimposed on the dark charges, it is not possible to separate them from each other and extract only the dark charges. Resetting dark charges during radiation irradiation or in the interval from the end of radiation irradiation to image signal readout operation will result in losing image signals. It is therefore necessary to exclusively execute resetting of dark charges and radiation irradiation. For this purpose, there is provided a mechanism for synchronizing the radiation imaging apparatus with the radiation irradiation apparatus. Japanese Patent Laid-Open No. 2003-33340 discloses a radiation imaging system including such a mechanism.

Starting to irradiate the pixels on the sensor array with radiation will generate charges inside the pixels and flow out to the bias lines connected to the respective pixels, resulting in a rapid increase in the amount of current in each bias line. For example, Japanese Patent Laid-Open No. 2009-219538 has proposed a radiation imaging apparatus which detects the start or the like of radiation by detecting a change in this amount of current.

In addition, as described above, since dark charges are always generated on the sensor array, it is necessary to periodically reset dark charges. For this reason, as shown in FIG. 1, the sensor array is configured to detect a change in the amount of current in each bias line while performing the reset scanning (TC101) of sequentially driving the respective rows (L0 to L10, . . . ) on the sensor array to turn on the switch elements so as to reset charges in the respective pixels connected to the corresponding rows. At the moment of the detection of the start of radiation, the sensor array stops the reset scanning on the row on which it has executed reset scanning (TC102), and turns off the switch element to shift the sensor driving state to the state of accumulating operation for image signal charges originating from radiation (TC103). In this state, the sensor array detects radiation.

Upon completion of radiation irradiation, the sensor array sequentially drives the respective rows to turn on the switch elements to shift the sensor driving state to the state of output operation for image signal charges, thereby reading out the radiation image signals accumulated in the respective pixels (TC104).

In this case, each pixel on the row in the process of reset operation at the time point (TC102) when the start of radiation irradiation is detected lets part of effective image signal charges generated by radiation irradiation flow out because the switch element is in the ON state.

In addition, in the radiation irradiation apparatus, if the dose of radiation does not instantly rise to the operating level at the start of radiation irradiation but gradually rises, the radiation imaging apparatus may detect the start of irradiation with a delay. In this case, the sensor array performs reset scanning on a plurality of rows (L2 to L7 in the case shown in FIG. 1) from the row corresponding to the time point when the radiation irradiation apparatus has actually started irradiation to the row corresponding to the time point when the radiation imaging apparatus has detected the start of irradiation. As a consequence, effective image signal charges accumulated over a plurality of rows by radiation irradiation partly flow out.

As shown in FIG. 2, the pixel values on the rows (L2 to L7) from which effective charges flow out are smaller in charge amount than those on preceding and succeeding rows (L0, L1, L8 to L10, . . . ), and hence lack in reliability. This makes it necessary to perform correction processing such as data interpolation. For example, the apparatus disclosed in Japanese Patent Laid-Open No. 2011-249891 is configured to wait for the detection of the start of radiation irradiation while sequentially performing the above reset scanning (TC301) on rows which are not physical adjacent to each other as shown in FIG. 3. According to this, there is provided a method of preventing rows (L2, L4, L6, and L8) on which data defects occur at the time of the detection of radiation from consecutively appearing, as shown in FIG. 4, and interpolating data on the defective rows from data on the preceding and succeeding normal rows, thereby improving the correction processing accuracy of image data. If, for example, a defective row is L2, interpolation processing is performed by using the preceding and succeeding normal rows (L1 and L3).

In addition, the radiation imaging system is required to be capable of displaying a captured image immediately after the execution of imaging in order to quickly determine whether imaging has been normally performed (re-imaging is required). However, a captured image requires various types of image correction processing such as offset correction processing for correcting offset components in the image and the transfer time required to transfer the image to the display device, resulting in a delay time (display delay time) from imaging to the display of the image.

For example, Japanese Patent Laid-Open No. 2012-152340 discloses a method of transferring a preview image to a display device upon offset correction to reduce the display delay time.

As disclosed in Japanese Patent Laid-Open Nos. 2009-219538 and 2011-249891, when the radiation imaging apparatus is configured to detect the start of radiation irradiation by itself, image data deteriorates due to data defects at the time of the detection of radiation on reset rows and their nearby rows at the time of the detection of the start of radiation irradiation. When displaying an obtained image as a preview image in advance upon reduction or the like, displaying an image deterioration at the time of the detection of radiation may make it impossible for the operator to determine whether imaging has been normally performed. This may make it necessary to perform re-imaging.

For this reason, in order to correct a deterioration in image data, it is necessary to perform image correction processing. If, however, image correction is also performed for a preview image, a time loss for correction processing occurs. This makes it impossible to quickly display an image.

SUMMARY OF THE INVENTION

The present invention provides a radiation imaging technique which can reduce a display delay concerning a image and display the image without performing correction processing for an image deterioration at the time of the detection of radiation.

According to one aspect of the present invention, there is provided a radiation imaging apparatus including a radiation detection unit including a radiation detection array having a plurality of pixels configured to detect radiation and accumulate charges and arranged two-dimensionally and a plurality of scanning lines for discharging charges accumulated in the pixels, the apparatus comprising: a reset control unit configured to perform reset scanning to sequentially discharge charges accumulated in the pixels; an irradiation detection unit configured to detect the start of radiation irradiation based on charges discharged by the reset scanning; an imaging control unit configured to perform control to stop the reset scanning in accordance with detection of the start of irradiation and obtain an image signal by reading out charges accumulated in the pixels by the radiation irradiation; a generation unit configured to generate image data based on the image signal except for an image signal from a pixel on which the reset scanning is performed during the radiation irradiation; and an output unit configured to output the image data to an external apparatus.

According to the present invention, it is possible to reduce a display delay concerning an image and display the image without performing correction processing for an image deterioration at the time of the detection of radiation.

Further features of the present invention will become apparent from the following description of exemplary embodiments (with reference to the attached drawings).

BRIEF DESCRIPTION OF THE DRAWINGS

FIG. 10 is a view for explaining image defects when the start of irradiation is detected on the first row;

FIG. 11 is a view for explaining an imaging sequence according to the second embodiment;

FIG. 13 is a view for explaining an imaging sequence according to the fourth embodiment; and FIG. 14 is a view for explaining an imaging sequence according to the fifth embodiment;

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

Figure 5:
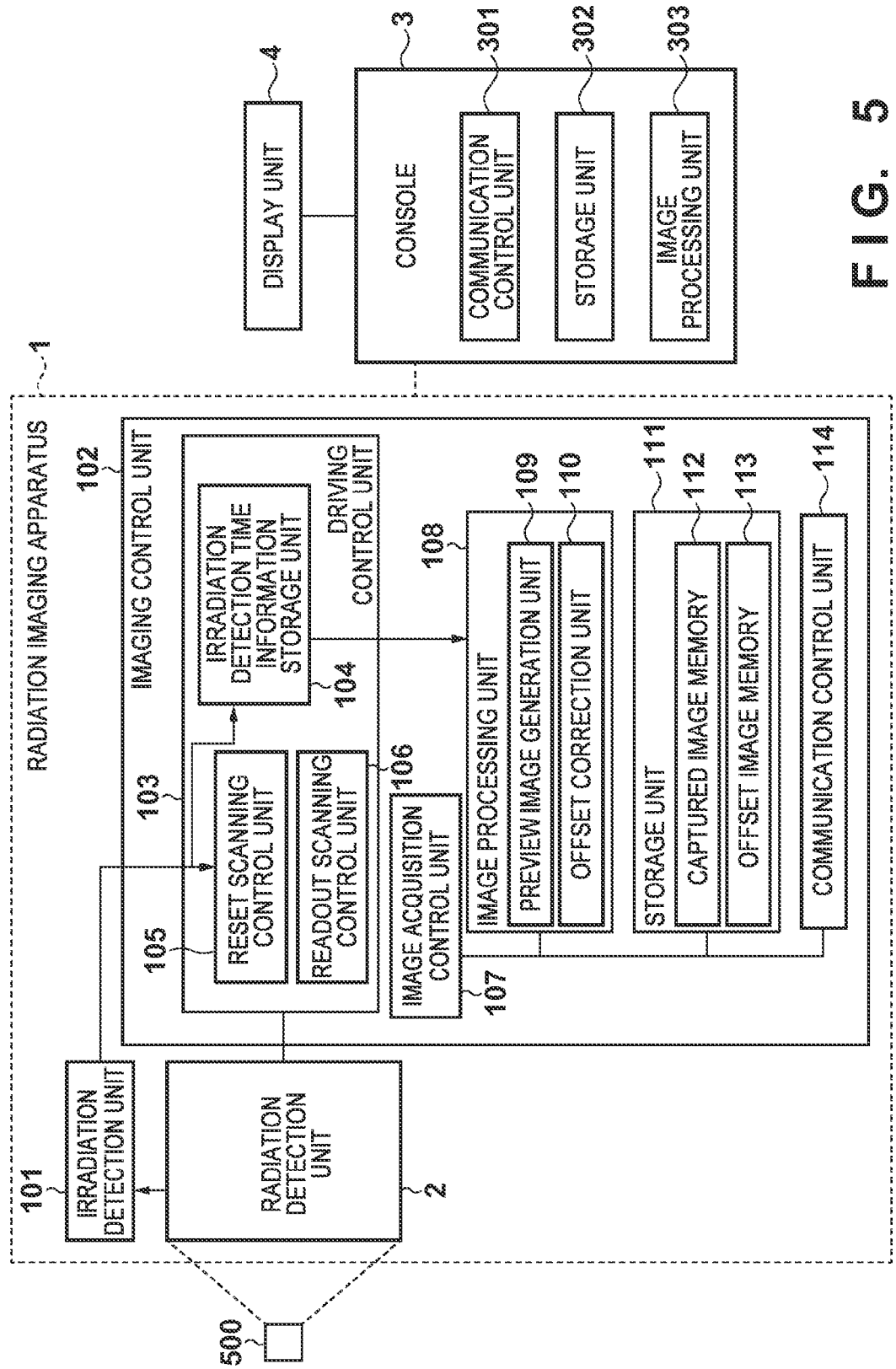
FIG. 5 is a block diagram showing an example of the arrangement of a radiation imaging system according to an embodiment.

FIG. 5 is a block diagram showing an example of the arrangement of a radiation imaging system according to an embodiment of the present invention. The radiation imaging system includes a radiation imaging apparatus 1, a console 3 (information processing apparatus) which controls the radiation imaging apparatus 1, a display unit 4, and a radiation generation unit 500 which irradiates an object with radiation. The radiation imaging apparatus 1 also includes a radiation detection unit 2 which generates image data by detecting radiation, an irradiation detection unit 101 which detects the start or end of radiation irradiation, and an imaging control unit 102 which controls imaging operation.

The imaging control unit 102 includes a driving control unit 103 which controls the scanning driving of the radiation detection unit 2, an image acquisition control unit 107 which controls the acquisition of image data from the radiation detection unit 2, and an image processing unit 108 which performs signal processing such as offset correction and preview image generation. The imaging control unit 102 includes a storage unit 111 storing the obtained image obtained from the radiation detection unit 2 and a communication control unit 114 which controls data communication with the console 3, for example, transferring an obtained image to the console 3 outside the apparatus. The communication control unit 114 can use, for example, wireless LAN communication for data communication between the radiation imaging apparatus 1 and the console 3. Note that data communication is not limited wireless LAN communication, and wireless communication of another system or wired communication using a cable may be used.

The driving control unit 103 includes a reset scanning control unit 105 for discharging (resetting) accumulated dark charges from the radiation detection unit 2 periodically or at an arbitrary timing. The driving control unit 103 includes a readout scanning control unit 106 which performs driving control to read out an image from the radiation detection unit 2, and an irradiation detection time information storage unit 104 for storing information concerning an irradiation time such as the number of the row on which reset scanning has been performed at the time point when radiation irradiation has started.

The console 3 includes a communication control unit 301 which controls data communication between the radiation imaging apparatus 1 and the console 3, for example, receiving the captured image transferred from the radiation imaging apparatus 1. The console 3 includes a storage unit 302 for storing the reception image transferred and received from the radiation imaging apparatus 1 and an image processing unit 303 for correcting a reception image.

The imaging control unit 102 reads out, for example, programs and the like saved in the storage unit 111, and performs overall control on the radiation imaging apparatus 1 based on the readout programs and the like. The imaging control unit 102 may control the radiation imaging apparatus 1 by performing apparatus control using a control signal generation circuit (control circuit) such as an ASIC or may implement overall control on the radiation imaging apparatus 1 by using both programs and the control circuit.

In the radiation detection unit 2, a plurality of conversion elements which convert radiation into charges are arranged along scanning lines in the row direction, and a plurality of scanning lines are arranged in the column direction. For example, the radiation detection unit 2 is formed by arranging, in a two-dimensional array, pixels each including a switch element such as a TFT and a photoelectric conversion element (radiation detection element). A phosphor is provided on each pixel. In this case, radiation entering the radiation detection unit 2 is converted into visible light by the phosphor and strikes the photoelectric conversion element of each pixel. Each photoelectric conversion element then generates charges in accordance with the visible light. Note that this embodiment will exemplify a "conversion element" as an arrangement example, which converts incident radiation into charges through the phosphor and photoelectric conversion element described above. Note however that the scope of the present invention is not limited to this arrangement example. For example, it is possible to use a so-called direct conversion type conversion element which directly converts incident radiation into charges without providing any phosphor. The radiation detection unit 2 can obtain a radiation image by executing charge accumulation and charge readout operation by switching on and off the TFTs.

Figure 6:
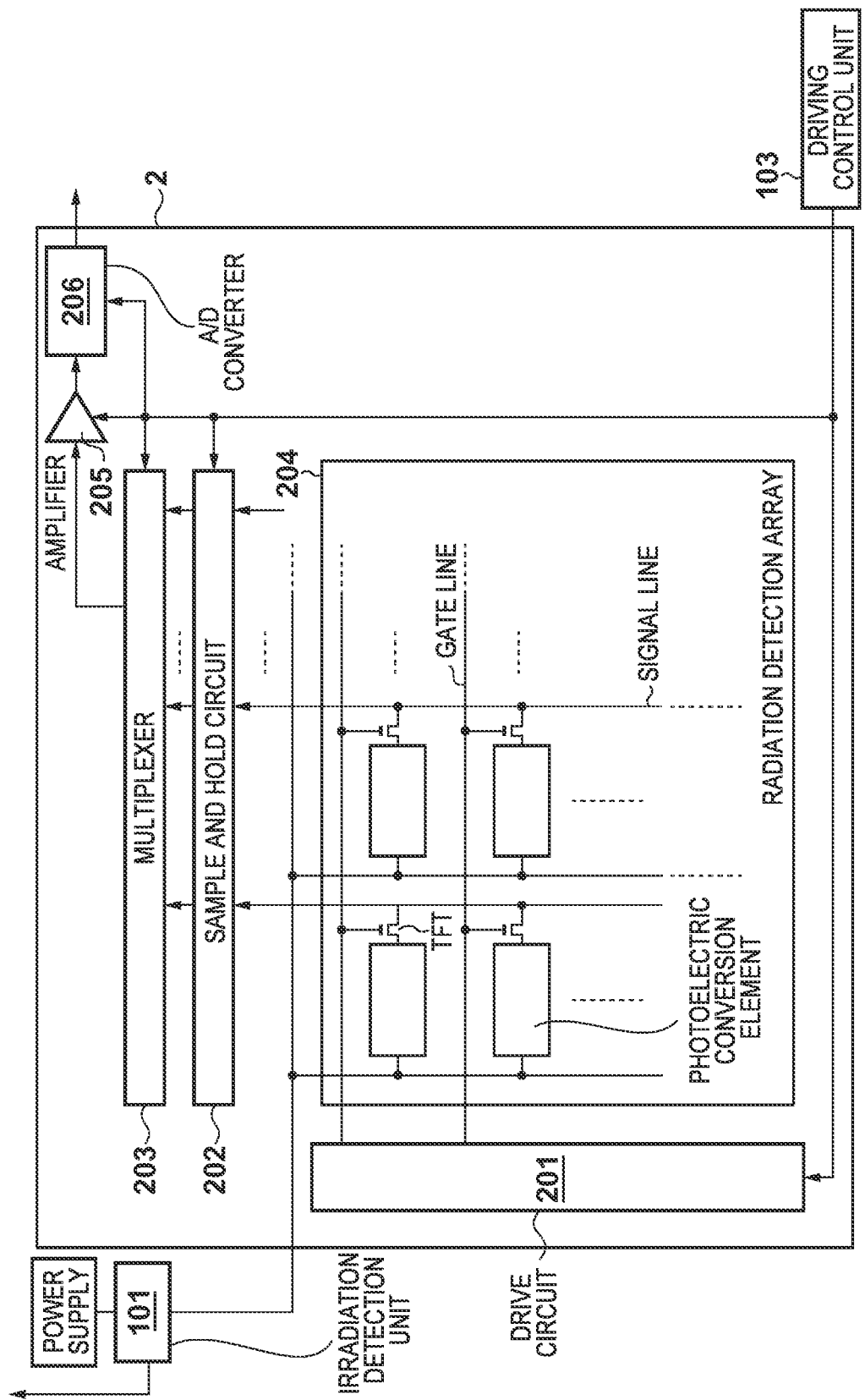
FIG. 6 is a block diagram showing an example of the arrangement of a radiation detection unit.

FIG. 6 is a block diagram showing an example of the arrangement of the radiation detection unit 2. A drive circuit 201 simultaneously addresses the respective pixels on a row on the two-dimensional sensor array of the radiation detection unit 2. A sample and hold circuit 202 holds charges from the respective pixels on the row. Thereafter, a multiplexer 203 sequentially reads out the charges (pixel outputs) from the respective pixels which are held by the sample and hold circuit 202. An amplifier 205 amplifies the readout charges. An A/D converter 206 then converts the charges into image data with a digital value. Every time scanning on each row is complete, the drive circuit 201 sequentially performs scanning by driving each next row on the two-dimensional sensor array, and finally converts the charges output from all the pixels into digital values. This makes it possible to read out radiation image data. In this case, the radiation detection unit 2 scans the respective pixels on a row while fixing a voltage applied to each column signal line connected to the pixels to a specific value, and discharges dark charges by discarding obtained charges, thereby discharging (resetting) the dark charges accumulated in the respective pixels. The driving control unit 103 performs control operation such as driving of the detection unit and readout operation.

If the image data converted into digital values by the A/D converter 206 is radiation image data obtained by radiation irradiation, a captured image memory 112 stores the radiation image data in FIG. 5. If the above image data is offset image data obtained from dark charge components from the respective pixels without performing radiation irradiation, an offset image memory 113 in FIG. 5 stores the offset image data.

An offset correction unit 110 included in the image processing unit 108 can obtain a captured image from which unnecessary dark charge components are removed by performing the offset correction of subtracting offset image data components from radiation image data.

The irradiation detection unit 101 which detects the start and end of radiation irradiation can include an independent sensor for radiation detection other than the radiation detection unit 2 which obtains images. For example, the radiation detection unit 2 can implement detection of the start and end of irradiation by itself by monitoring the amount of dark charges discharged during reset scanning on the radiation detection unit 2.

Offset image data is obtained, for example, after radiation imaging. The offset correction unit 110 then performs offset correction. Note that the acquisition timing of offset image data is not limited to that after radiation imaging. For example, offset image data may be obtained before radiation imaging. Alternatively, if variations in dark charges are small, one offset image prepared in advance may be repeatedly used for offset correction processing.

The image processing unit 108 in the radiation imaging apparatus 1 also includes a preview image generation unit 109 which generates a preview image by reducing a captured image from which unnecessary dark charge components are removed. For example, the preview image generation unit 109 generates a preview image in advance from a radiation captured image before offset correction after the acquisition of the captured image. The preview image generation unit 109 then transfers the preview image generated in advance to the console 3 under the control of the communication control unit 114 to allow the display unit 4 connected to the console 3 to display the preview image generated in advance. Thereafter, the captured image for which offset correction is executed by the offset correction unit 110 and which is not reduced is transferred to the console 3 under the control of the communication control unit 114. The display unit 4 connected to the console 3 displays the transferred captured image as an actual image.

The communication control unit 301 of the console 3 controls data transmission/reception with respect to the radiation imaging apparatus 1. For example, the communication control unit 301 controls data transmission/reception with respect to the imaging control unit 102 by operating software incorporated in a computer or the like to set parameters such as an imaging region and imaging conditions. The image processing unit 303 of the console 3 performs image processing to form the captured image received from the radiation imaging apparatus 1 into a shape suitable for diagnosis. In addition, the storage unit 302 of the console 3 stores the captured image received from the radiation imaging apparatus 1. The display unit 4 displays the radiation captured image based on the charges read out from the radiation detection unit 2, an operation UI, and the like based on the captured image data transmitted to the console 3.

Figure 7:
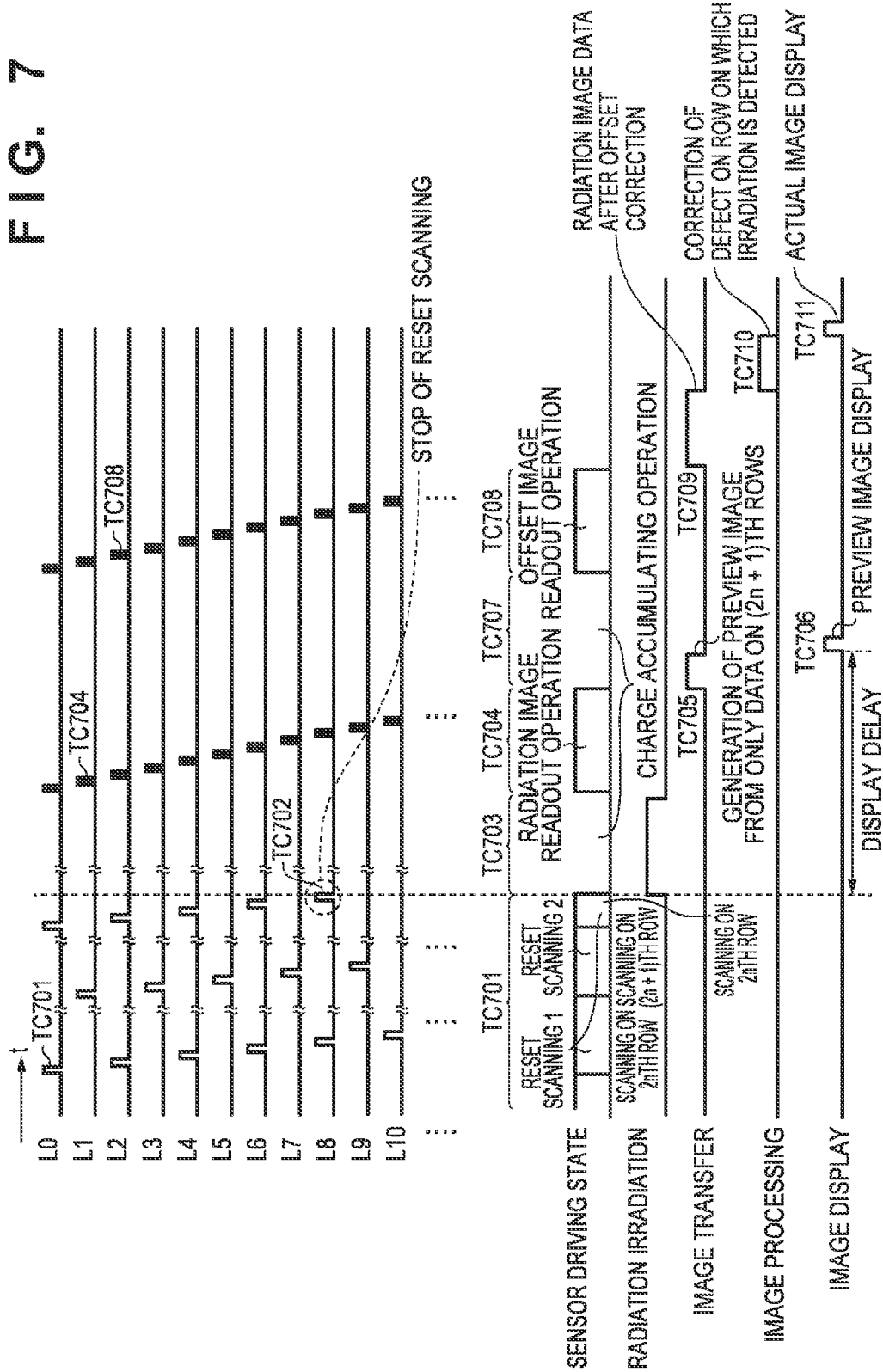
FIG. 7 is a view for explaining an imaging sequence in the radiation imaging system.
Figure 8:
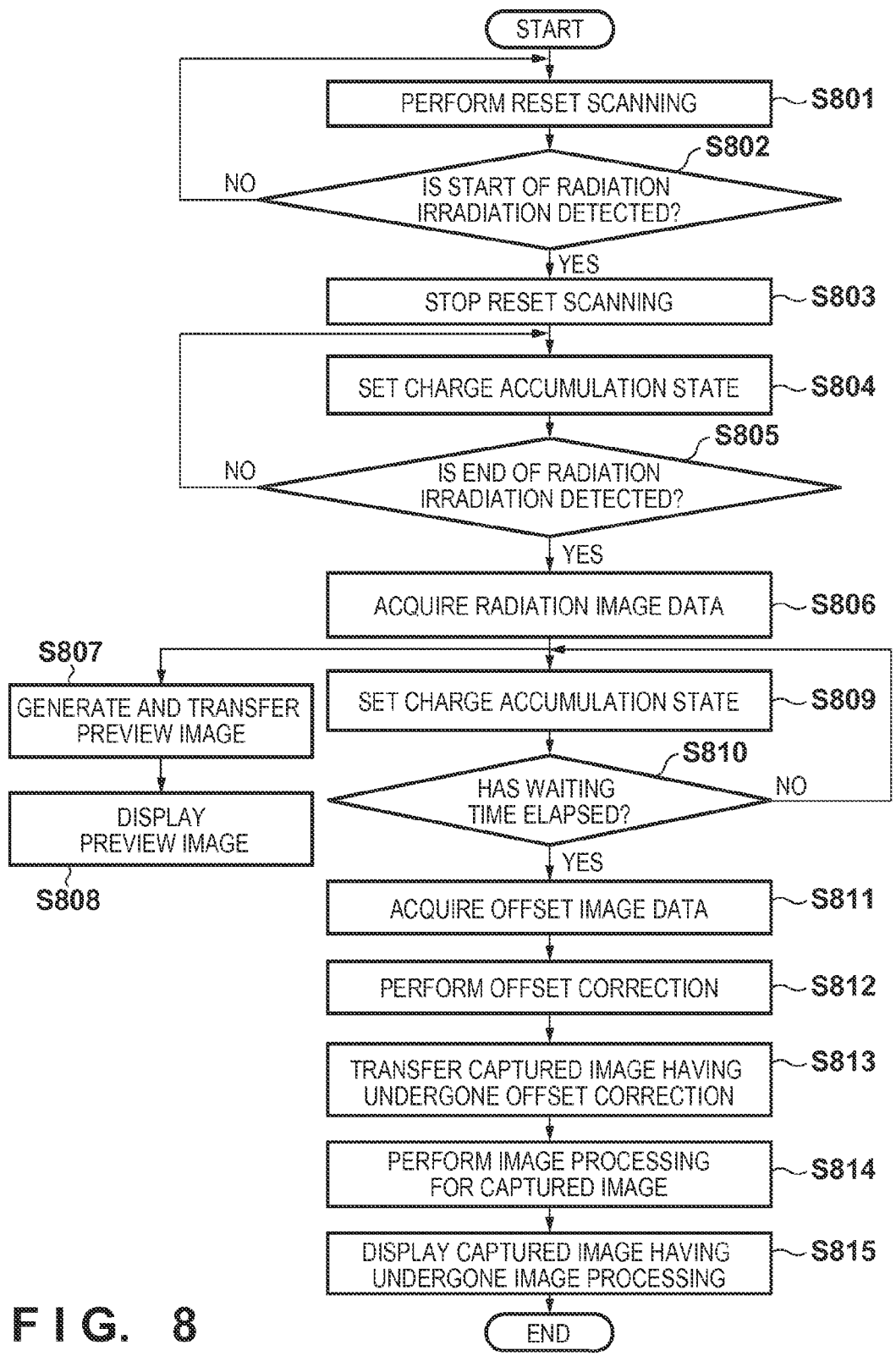
FIG. 8 is a view for explaining an imaging sequence in the radiation imaging system.

FIG. 7 is a timing chart showing an imaging sequence in the radiation imaging system according to this embodiment. FIG. 8 is a flowchart for explaining a procedure for an imaging sequence in the radiation imaging system. The operation of the radiation imaging system will be described with reference to FIGS. 7 and 8.

When the radiation imaging apparatus starts up and enters the standby state for imaging, the reset scanning control unit 105 of the driving control unit 103 periodically executes reset scanning to prevent dark charges from being accumulated in the two-dimensional sensor array forming the radiation detection unit 2 (TC701 in FIG. 7 and step S801 in FIG. 8). In this case, the reset scanning control unit 105 selects scanning lines as reset scanning targets so as to sequentially perform reset scanning (TC701) on conversion elements on rows (scanning lines) which are not physically adjacent to each other on the two-dimensional sensor array, and sequentially drives the conversion elements on the selected scanning lines. For example, in the first partial reset scanning, the reset scanning control unit 105 sequentially selects the (2×n)th rows (n is incremented one by one from n=0) and scans the selected rows (L0, L2, L4, . . . . ) In the second partial reset scanning, the reset scanning control unit 105 sequentially selects the (2×n+1)th rows (n is incremented one by one from n=0) and scans the selected rows (L1, L3, L5, . . . . ) The reset scanning control unit 105 waits for radiation irradiation while discharging dark charges by repeating the first partial reset scanning and the second partial reset scanning. Note that the selection order of reset scanning is a merely example, and the reset scanning control unit 105 may perform the second partial reset scanning first, and then perform the first partial reset scanning after the second partial reset scanning.

In addition, this embodiment exemplifies the case in which the reset scanning control unit 105 scans every other row as rows (scanning lines) which are not adjacent to each other. However, the scope of the present invention is not limited to this. When, for example, scanning every two rows as rows (scanning lines) which are not adjacent to each other, the reset scanning control unit 105 scans the (3×n)th row in the first partial reset scanning, scans the (3×n+1)th row in the second partial reset scanning, and scans the (3×n+2)th row in the third partial reset scanning.

In addition, when scanning every three row, the reset scanning control unit 105 scans the (4×n)th row in the first partial reset scanning, scans the (4×n+1)th row in the second partial reset scanning, scans the (4×n+2)th row in the third partial reset scanning, and scans the (4×n+3)th row in the fourth partial reset scanning. In this manner, the reset scanning control unit 105 may scan every arbitrary number (m−1: m is an integer equal to or more than 2) of rows and may repeat reset scanning up to the mth partial reset scanning.

In addition, the reset scanning control unit 105 may select a plurality of rows and perform reset scanning on them at once as long as they are not adjacent rows. When, for example, scanning every three rows, the reset scanning control unit 105 may simultaneously select rows and perform reset scanning on them in the first partial reset scanning and the third partial reset scanning. In addition, the reset scanning control unit 105 may simultaneously select rows and perform reset scanning on them in the second partial reset scanning and the fourth partial reset scanning.

In step S802, the irradiation detection unit 101 determines whether the radiation generation unit 500 has started radiation irradiation. If the irradiation detection unit 101 does not detect the start of radiation irradiation (NO in step S802), the reset scanning control unit 105 repeatedly executes reset scanning (step S801).

When the radiation generation unit 500 irradiates radiation upon operation input by the user, the irradiation detection unit 101 detects this. If the irradiation detection unit 101 detects the start of radiation irradiation (YES in step S802), the reset scanning control unit 105 stops reset scanning (TC702 and step S803). The readout scanning control unit 106 turns off all the TFT switches on the two-dimensional sensor array, and sets all the pixels on the two-dimensional sensor array in the charge accumulation state (TC703 and step S804). When the reset scanning control unit 105 stops reset scanning, the sensor driving state shifts to the charge accumulation state.

At this time, the driving control unit 103 stores information on the two-dimensional sensor array at the time of the stop of reset scanning in the irradiation detection time information storage unit 104. That is, the driving control unit 103 stores, in the irradiation detection time information storage unit 104, information concerning a row number corresponding to the time when reset scanning is stopped, the type of partial reset scanning when reset scanning is stopped, an output value corresponding to the time when irradiation is detected, and the like. Referring to FIG. 7, the row number corresponding to the time when reset scanning is stopped is 8 (L8). In this case, the type of partial reset scanning indicates information for selecting rows (scanning lines) which are not adjacent to each other at the time of the execution of reset scanning, for example, information indicating scanning on every other row, scanning on every two rows, or scanning on every three rows.

In step S805, the irradiation detection unit 101 determines whether radiation irradiation is complete. If radiation irradiation is not complete (NO in step S805), the apparatus continues charge accumulating operation (TC703 and step S804).

If the irradiation detection unit 101 detects the end of radiation irradiation (YES in step S805), the readout scanning control unit 106 turns off all the TFT switches on the two-dimensional sensor array to set all the pixels on the two-dimensional sensor array in the charge output state. To read out the charges accumulated by radiation irradiation, the readout scanning control unit 106 performs readout scanning control (TC704) to sequentially scan rows on the two-dimensional sensor array, and obtains radiation image data captured by radiation (step S806). The captured image memory 112 stores the radiation image data obtained in this case.

As described in "Description of the Related Art", radiation image data can deteriorate in quality on some rows due to a detection delay from the start of actual radiation irradiation to the detection of the start of irradiation by the irradiation detection unit 101. When displaying a preview image, in order to reduce the influence of a deterioration in image data, the readout scanning control unit 106 obtains information concerning the two-dimensional sensor array at the time of the stop of reset scanning, which is stored in the irradiation detection time information storage unit 104. The readout scanning control unit 106 then specifies defective image data of the radiation image data.

Figure 4:
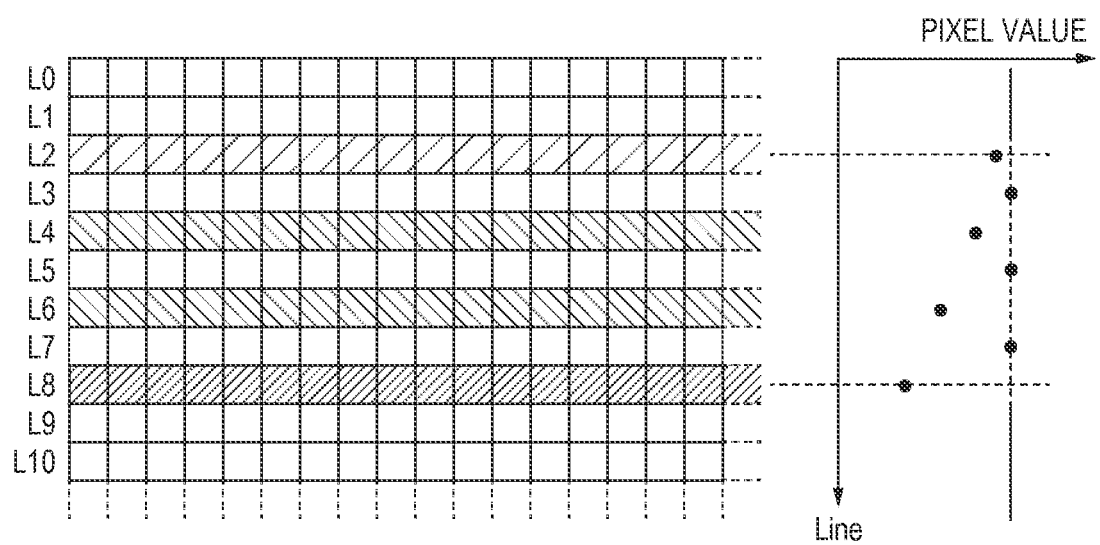
FIG. 4 is a view for explaining image defects obtained by conventional reset scanning.

Referring to FIG. 7, the irradiation detection unit 101 detects the start of radiation irradiation during partial reset scanning on the (2×n)th row. Therefore, as shown in FIG. 4, defects have occurred in radiation image data on the reset row (L8) corresponding to the time when reset scanning is stopped and the preceding (2×n)th rows (L2, L4 and L6).

Note that, with regard to the radiation irradiation end timing, the irradiation detection unit 101 may detect the end of radiation irradiation, or the imaging control unit 102 may start readout operation upon standing by for a specific fixed time, with the corresponding timing being regarded as the end of irradiation. When the two-dimensional sensor array detects the end of irradiation by itself, it is possible to detect the end of irradiation by, for example, keeping the TFT switch on on the row on which reset scanning has been performed at the start of irradiation without turning the TFT switch off, and keeping monitoring the amount of current flowing in the bias line.

The preview image generation unit 109 of the image processing unit 108 decides image data to be used for the generation of a preview image. No image deterioration has occurred in image data on the (2×n+1)th rows selected in the second partial reset scanning, on which no reset scanning has been performed at the start of radiation irradiation, because no effective charges flow out by reset. The preview image generation unit 109 of the image processing unit 108 decides image data on rows other than the rows selected in the partial reset scanning executed at the time of the detection of the start of irradiation as image data to be used for the generation of a preview image, and generates a preview image from the image data (TC705 and step S807). The communication control unit 114 transfers the preview image generated by the preview image generation unit 109 to the console 3 before an actual image for diagnosis (TC705 and step S807).

The preview image transferred to the console 3 requires no deteriorated image correction processing because there is no image deterioration at the time of the detection of irradiation, and can be instantaneously displayed on the display unit 4 (TC706 and step S808).

Figure 9:
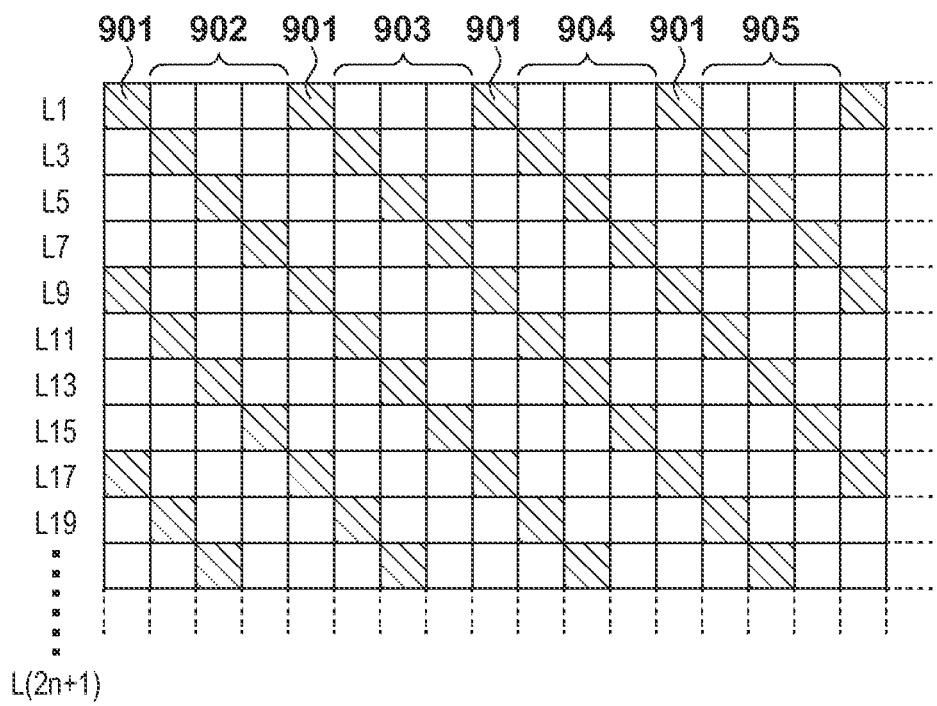
FIG. 9 is a view for exemplarily explaining thinning-out of a preview image.

In this case, when the preview image generation unit 109 of the image processing unit 108 generates a preview image, the preview image generation unit 109 may generate a preview image by further thinning out and reducing data on rows other than rows selected in partial reset scanning at the time of the detection of irradiation (image data on the (2×n+1)th row). When generating thinned-out reduced image data, the preview image generation unit 109 can generate a reduced preview image by reducing a captured image by thinning out pixels as shown in FIG. 9 and then transfer the image to the console 3. Referring to FIG. 9, on a row L1, a hatched pixel 901 is used for the generation (sampling) of a reduced preview image, and blanked pixels 902 to 905 are thinned out.

As shown in FIG. 9, starting sampling from physically consecutive pixels can reduce, by thinning-out, the influence of specific frequency noise such as a periodic signal (grid stripe) corresponding to the arrangement of a grid for removing scattered radiation on an object. Note that, with regard to a method of generating a reduced preview image by using the preview image generation unit 109, the method to be used is not limited to that exemplified by FIG. 9, and another thinning-out method can be used. For example, the preview image generation unit 109 may generate a reduced preview image by using interpolation processing among pixels to be used for the generation of a reduced preview image. It is also possible to generate a reduced preview image by combining the pixel values of pixels used for the generation of a reduced preview image with interpolation processing. Note that the thinning-out ratio to be set is not limited to that exemplified in FIG. 9, and various ratios can be set.

Upon completing the readout operation for the radiation image data (step S806), the readout scanning control unit 106 turns off the TFT switches of all the pixels on the two-dimensional sensor array to set the charge accumulation state (TC707 and step S809). The readout scanning control unit 106 executes the processing in this step concurrently with the generation/transfer processing of a preview image (TC705 and step S807) and preview image display processing (TC706 and step S808) described above. Performing concurrent processing in this manner can shorten the time from the generation and display of a preview image to the generation and display of an actual image for diagnosis (to be described later).

In step S810, the readout scanning control unit 106 determines whether the same waiting time as the accumulation time at the time of radiation irradiation (TC703 and step S804) has elapsed (the waiting time has elapsed). If this waiting time has not elapsed (NO in step S810), the readout scanning control unit 106 continues charge accumulating operation. This continues the accumulation of dark charges. Upon determining that the same time as the accumulation time at the time of radiation irradiation has elapsed (YES in step S810), the readout scanning control unit 106 turns on all the TFT switches on the two-dimensional sensor array to set all the pixels on the two-dimensional sensor array in the charge output state. The readout scanning control unit 106 then executes readout operation to obtain the offset image data of only dark charge components (TC708 and step S811).

Subsequently, the offset correction unit 110 performs offset correction by using all the radiation image data stored in the captured image memory 112 and the obtained offset image data (step S812). The offset correction unit 110 obtains a captured image from which dark charge components are removed by the offset correction of subtracting offset image data components from the radiation image data.

The communication control unit 114 transfers the captured image, for which offset correction has been performed by the offset correction unit 110, as an actual image to the console 3 (TC709 and step S813).

Unlike a preview image, a captured image deteriorates in data near a reset row at the time of the detection of irradiation, and hence needs to correct it. For this reason, the driving control unit 103 reads out, from the irradiation detection time information storage unit 104, information (information at the time of the detection of irradiation) concerning the two-dimensional sensor array at the time of the stop of reset scanning. The communication control unit 114 transfers the information at the time of the detection of irradiation, read out by the driving control unit 103, to the console 3.

The image processing unit 303 of the console 3 specifies, from the information at the time of the detection of irradiation, information concerning a row number corresponding to the time when reset scanning is stopped, the type of partial reset scanning when partial reset scanning is stopped (a method of selecting rows (scanning lines) which are not adjacent to each other), an output value corresponding to the time when irradiation is detected, and the like. The image processing unit 303 performs image correction so as to interpolate defects in the received captured image by using the specified information and performs image processing suitable for each type of diagnosis (TC710 and step S814). The display unit 4 displays the captured image for which image processing has been performed by the image processing unit 303 (TC711 and step S815: display of actual image).

Note that in this embodiment, the image processing unit 303 of the console 3 executes image defect correction processing at the time of the detection of irradiation. However, the present invention is not limited to this, and the image processing unit 108 in the radiation imaging apparatus 1 may execute this processing. In this case, it is not necessary to transfer the information at the time of the detection of irradiation to the console 3, and the image processing unit 108 may perform correction processing by using the information.

If a reset row at the time of the detection of the start of radiation irradiation is located near the head of a row selected by partial reset scanning, an image deterioration due to an irradiation start detection delay may also appear across the vicinity of the last row on which partial reset scanning has been executed at the immediately preceding timing. As shown in FIG. 10, if a reset row at the time of the detection of the start of irradiation is the first row (L0) at the time of the first partial reset scanning, an image deterioration also appears across the vicinity of the last row (L2(n−2)+1, L2(n−1)+1, and L2n+1)) in the second partial reset scanning executed earlier. In this case, if no defect occurs, each pixel exhibits a pixel value 1001. If the first row (L0) at the time of first partial reset scanning is a reset row at the time of the detection of the start of radiation irradiation, a pixel value 1002 of the first row (L0) is much lower than the pixel value 1001 as a reference. A pixel value 1003 of a row L2(n−2)+1, a pixel value 1004 of a row L2(n−1)+1, and a pixel value 1005 of a row L2n+1 near the last row in the second partial reset scanning gradually decrease relative to the pixel value 1001 as the reference and approach the pixel value 1002 of the first row (L0).

Figure 1:
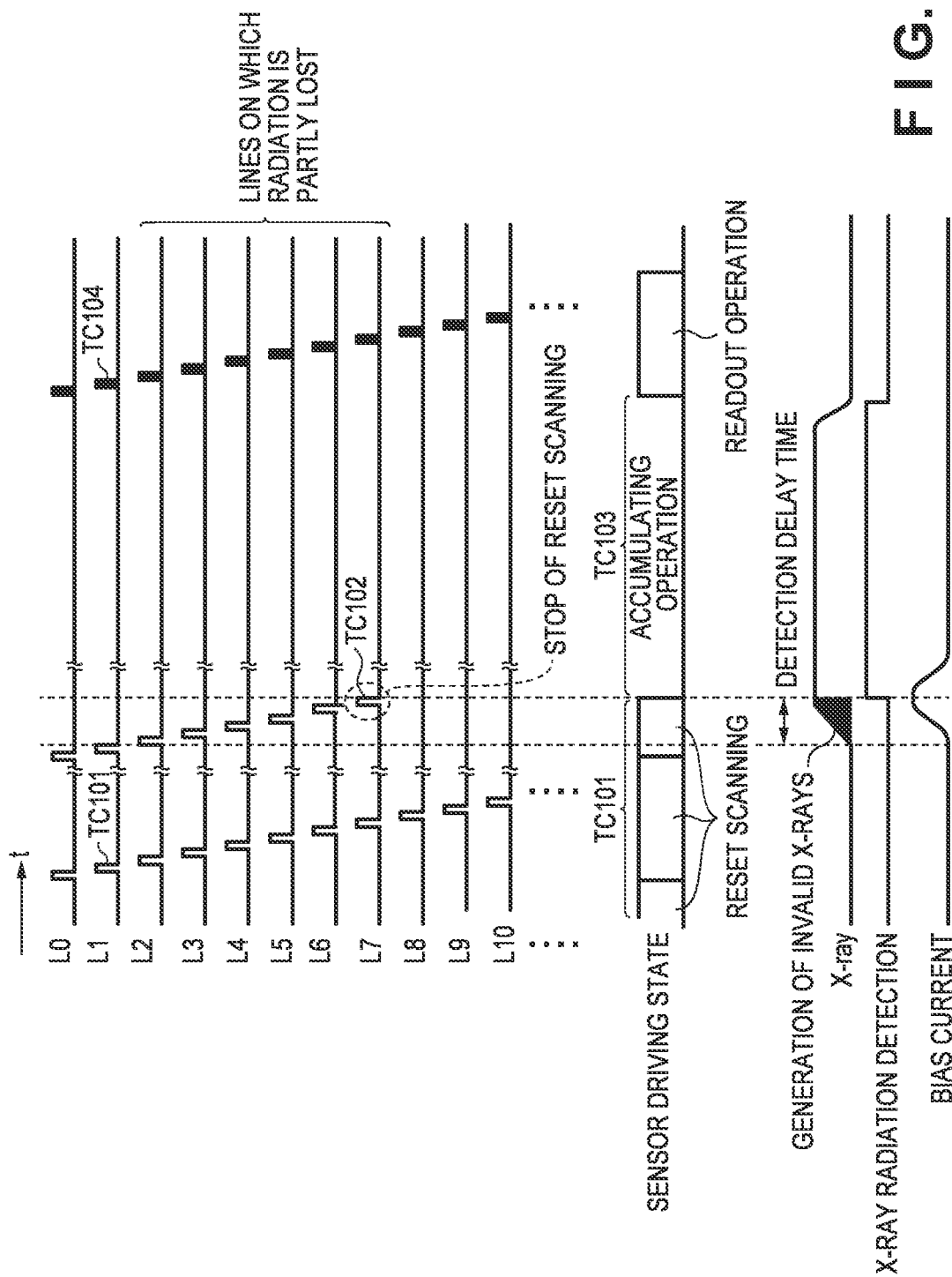
FIG. 1 is a timing chart for the detection of the start of radiation irradiation and the acquisition of a captured image.
Figure 2:
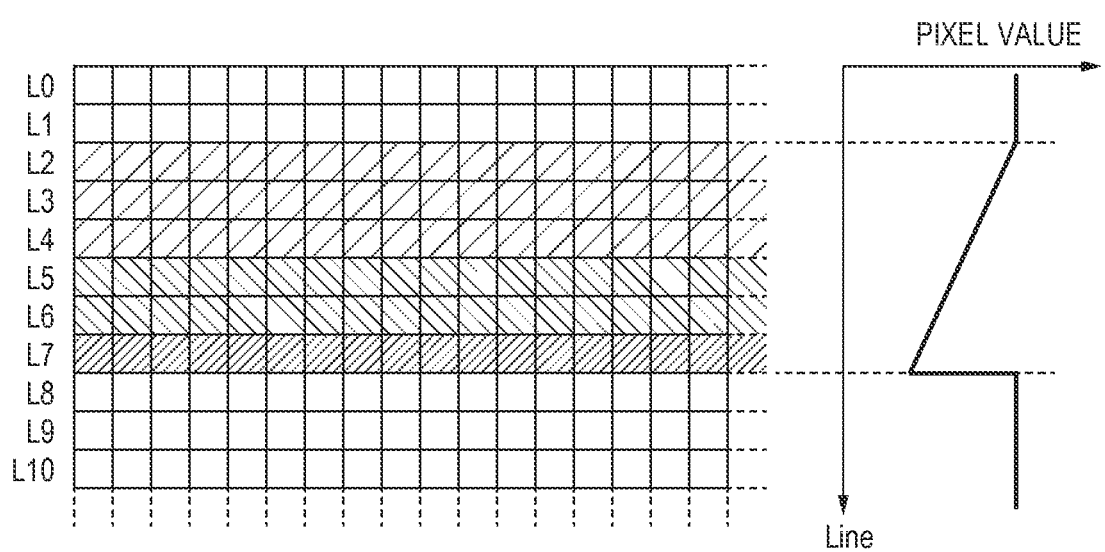
FIG. 2 is a view for explaining image defects caused by a delay in irradiation start detection.
Figure 3:
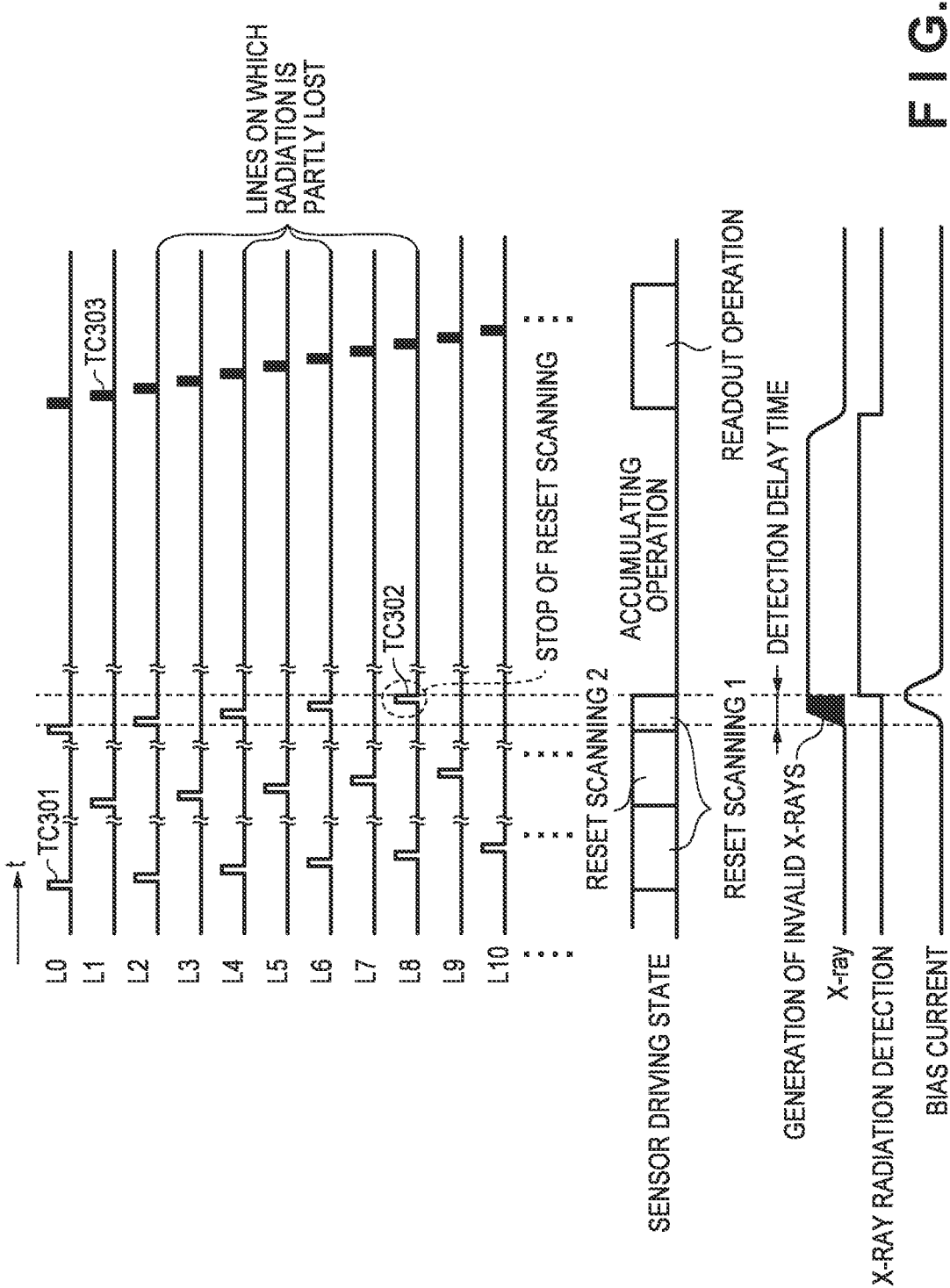
FIG. 3 is a view for explaining an imaging sequence using conventional reset scanning.

Note however that even in this case, a preview image is generated from image data on a row ((2×n+1)th row) selected in the second partial reset scanning but not subjected to reset scanning at the time of the detection of irradiation. A most noticeable image deterioration appears on a row (for example, L7 in FIG. 2) at the time of the stop of reset scanning, which exhibits the largest change in pixel value in the column direction and on which a level difference occurs. In the case shown in FIG. 10, although image deteriorations have also occurred in the image data on the (2×n+1)th row used as a preview image, they do not look as level differences but look as gradual gradation on an end portion. Therefore, they have little influence on the display of a preview image.

The radiation imaging apparatus according to this embodiment is the radiation imaging apparatus including the radiation detection unit 2 including a radiation detection array 204 having a plurality of pixels configured to detect radiation and accumulates charges and arranged two-dimensionally and a plurality of scanning lines for sequentially discharging the charges accumulated in the pixels on a line basis.

The reset scanning control unit 105 functioning as a reset control unit of the radiation imaging apparatus sequentially selects scanning lines which are not adjacent to each other and performs reset scanning. The irradiation detection unit 101 detects the start of radiation irradiation based on the charges discharged by reset scanning.

The imaging control unit 102 performs control to stop reset scanning in accordance with the detection of the start of irradiation and obtain image signals by reading out charges accumulated in the pixels of the radiation detection array 204 by radiation irradiation.

The preview image generation unit 109 functioning as a generation unit of the radiation imaging apparatus generates image data based on image signals from which image signals from scanning lines on which reset scanning has been performed during radiation irradiation are removed. The communication control unit 114 functioning as an output unit of the radiation imaging apparatus outputs image data to an external apparatus.

The imaging control unit 102 reads out charges, from which image signals are obtained, starting from the scanning line on which reset scanning is stopped.

The reset scanning control unit 105 sequentially selects scanning lines in accordance with a predetermined sequence. The imaging control unit 102 reads out charges, from which image signals are obtained, in accordance with a predetermined sequence, starting from the scanning line on which reset scanning is stopped. The preview image generation unit 109 generates image data based on image signals corresponding to the scanning line from which readout operation has started to the N/2th scanning line from which readout operation is performed, with N representing the total number of lines from which image signals are obtained.

The communication control unit 114 outputs the image data generated by the preview image generation unit 109 and then outputs another image data containing image signals from scanning lines on which reset scanning has performed during radiation irradiation to an external apparatus.

The reset scanning control unit 105 separately performs reset scanning on even-numbered lines and odd-numbered lines in accordance with a predetermined sequence. If a line on which reset scanning is stopped is an even-numbered line, the preview image generation unit 109 generates image data based on image signals from an odd-numbered line. If a line on which reset scanning is stopped is an odd-numbered line, the preview image generation unit 109 generates image data based on image signals from an even-numbered line.

The radiation imaging apparatus according to this embodiment is the radiation imaging apparatus including the radiation detection unit having the radiation detection array 204 having a plurality of pixels configured to detect radiation and accumulate charges and arranged two-dimensionally and a plurality of scanning lines for discharging the charges accumulated in the pixels.

The reset scanning control unit 105 functioning as a reset control unit of the radiation imaging apparatus performs reset scanning to sequentially discharge charges accumulated in the pixels of the radiation detection array 204. The irradiation detection unit 101 detects the start of radiation irradiation based on charges discharged by reset scanning. The imaging control unit 102 performs control to stop reset scanning in accordance with the detection of the start of irradiation and obtain image signals by reading out charges accumulated in the pixels of the radiation detection array 204 by radiation irradiation.

The preview image generation unit 109 functioning as a generation unit of the radiation imaging apparatus generates image data based on image signals from which image signals from pixels on which reset scanning has been performed during radiation irradiation are removed. The communication control unit 114 functioning as an output unit of the radiation imaging apparatus outputs image data to an external apparatus.

Second Embodiment

A radiation imaging system according to the second embodiment of the present invention will be described next. Since the arrangement of the radiation imaging system according to this embodiment is the same as that of the radiation imaging system according to the first embodiment described above, a description of each constituent element will be omitted.

Figure 12A:
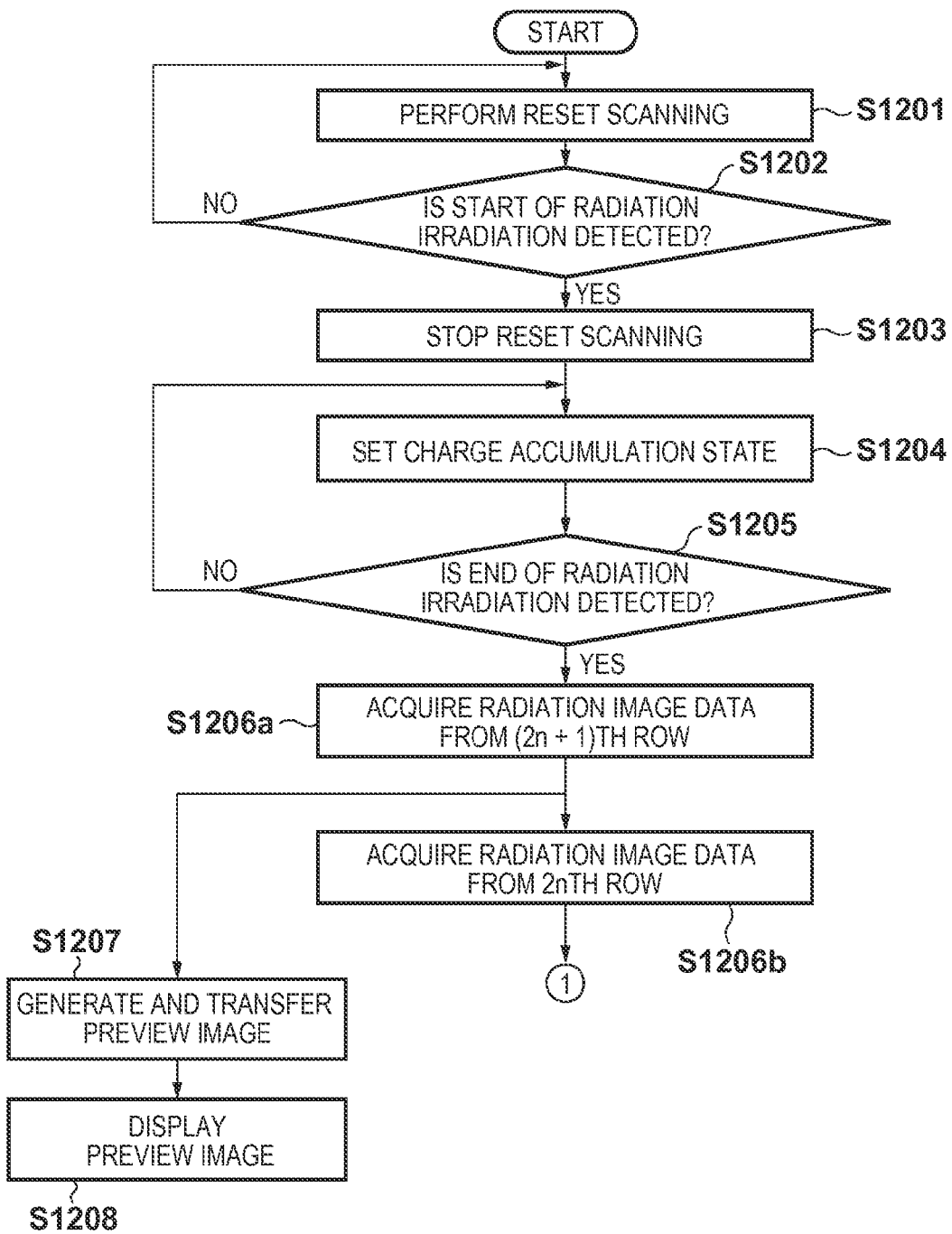
FIGS. 12A and 12B are flowcharts for explaining an imaging sequence according to the second embodiment.
Figure 12B:
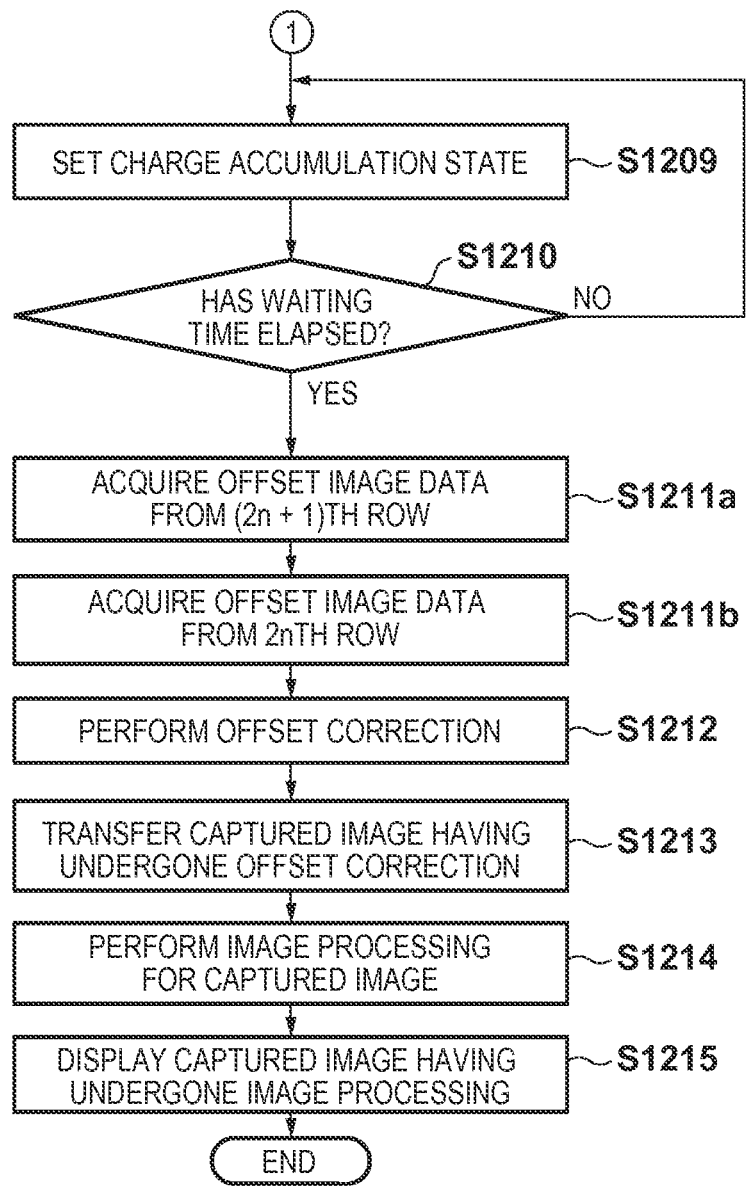

FIGS. 11, 12A and 12B are a timing chart and a flowchart, respectively, showing an imaging sequence in the radiation imaging system according to this embodiment. The operation of the radiation imaging system will be described with reference to FIGS. 11, 12A and 12B. In this embodiment as well, a reset scanning control unit 105 of a driving control unit 103 periodically executes reset scanning to prevent dark charges from being accumulated in a two-dimensional sensor array forming a radiation detection unit 2. The reset scanning control unit 105 selects scanning lines as reset scanning targets so as to sequentially perform reset scanning on rows (scanning lines) which are not physically adjacent to each other on the two-dimensional sensor array, and sequentially drives the conversion elements on the selected scanning lines (TC1101 and step S1201).

In step S1202, if an irradiation detection unit 101 does not detect the start of radiation irradiation (NO in step S1202), the reset scanning control unit 105 repeatedly executes reset scanning (step S1201). If the irradiation detection unit 101 detects the start of radiation irradiation (YES in step S1202), the reset scanning control unit 105 stops reset scanning (TC1102 and step S1203). A readout scanning control unit 106 turns off all the TFT switches on the two-dimensional sensor array to set all the pixels on the two-dimensional sensor array in the charge accumulation state (TC1103 and step S1204). In the case shown in FIG. 11, reset scanning stops during reset scanning 1 on the 2 nth row. The driving control unit 103 stores, in an irradiation detection time information storage unit 104, information concerning a row number corresponding to the time when reset scanning is stopped, the type of partial reset scanning when reset scanning is stopped, an output value corresponding to the time when irradiation is detected, and the like. The information stored in this case is used to read out radiation image data.

In step S1205, the irradiation detection unit 101 determines whether radiation irradiation is complete. If radiation irradiation is not complete (NO in step S1205), the readout scanning control unit 106 continues charge accumulating operation (TC1203 and step S1204).

If the irradiation detection unit 101 detects the end of radiation irradiation (YES in step S1205), the readout scanning control unit 106 turns on all the TFT switches on the two-dimensional sensor array to set all the pixels on the two-dimensional sensor array in the charge output state. To read out charges accumulated by radiation irradiation, the readout scanning control unit 106 performs readout scanning control to sequentially scan the rows on the two-dimensional sensor array (TC1104a and TC1104b), thereby acquiring radiation image data by radiation imaging (step S1206).

When executing readout scanning for a captured image, the readout scanning control unit 106 selects only a row (for example, the (2n+1)th row) other than the row (for example, the 2 nth row) selected in partial reset scanning at the time of the detection of irradiation, and executes readout scanning first.

For example, in the case shown in FIG. 10, the irradiation detection unit 101 has detected the start of irradiation at the time of the first partial reset scanning of sequentially performing reset scanning on the (2×n)th row. When performing readout scanning, the readout scanning control unit 106 performs partial readout scanning of sequentially reading out radiation image data, starting from the (2×n+1)th row other than the 2 nth row (TC1104a and step S1206a: first partial readout scanning).

Upon completion of readout of radiation image data from the (2×n+1)th row, the readout scanning control unit 106 performs partial readout scanning of sequentially reading out radiation image data from the (2×n)th row (TC1104b and step S1206b: second partial readout scanning). In this case, in the radiation image data obtained by the first partial readout scanning (TC1104a and step S1206a), there is no deterioration in radiation image data at the time of the detection of irradiation. Upon completion of the first partial readout scanning (TC1104a and step S1206a), therefore, a preview image generation unit 109 generates a preview image from the radiation image data obtained by the first partial readout scanning by concurrent processing with the second partial readout scanning (TC1105 and step S1207). A communication control unit 114 then transfers the preview image generated by the preview image generation unit 109 to a console 3 before an actual image for diagnosis (TC1105 and step S1207).

The preview image transferred to the console 3 is free from an image deterioration at the time of the detection of irradiation, and hence requires no deteriorated image correction processing and can be instantaneously displayed on a display unit 4 (TC1106 and step S1208). This makes it possible to transfer a preview image in advance without waiting for the completion of readout from all the rows on the sensor array. This embodiment can shorten the delay time until a preview image is displayed as compared with the first embodiment.

Upon completion of readout operation of radiation image data from the (2×n)th row (TC1104b and step S1206b), the readout scanning control unit 106 turns off the TFT switches of all the pixels on the two-dimensional sensor array again to set it in the charge accumulation state (TC1107 and step S1209).

In step S1210, the readout scanning control unit 106 determines whether the same time as the accumulation time at the time of radiation irradiation (TC1103 and step S1204) has elapsed (the waiting time has elapsed). If this waiting time has not elapsed (NO in step S1210), the readout scanning control unit 106 continues the charge accumulating operation. This continues the accumulation of dark charges. Upon determining that the same time as the accumulation time at the time of radiation irradiation has elapsed (YES in step S1210), the readout scanning control unit 106 turns on all the TFT switches on the two-dimensional sensor array to set all the pixels on the two-dimensional sensor array in the charge output state. The readout scanning control unit 106 then obtains offset image data of only dark charge components by executing readout operation.

At the time of readout scanning, the readout scanning control unit 106 sequentially reads out offset image data, starting from the (2×n+1)th row other than the 2 nth row (TC1108a and step S1211a).

Upon completion of readout of offset image data from the (2×n+1)th row, the readout scanning control unit 106 sequentially reads out offset image data from the (2×n)th row (TC1108b and step S1211b).

An offset correction unit 110 performs offset correction by using all the radiation image data stored in a captured image memory 112 and the obtained offset image data (step S1212). The offset correction unit 110 obtains a captured image from which dark charge components are removed by the offset correction of subtracting offset image data components from the radiation image data. The communication control unit 114 transfers the captured image for which offset correction has been performed by the offset correction unit 110, as an actual image, to the console 3 (TC1109 and step S1213).

The driving control unit 103 reads out information at the time of the detection of irradiation from an irradiation detection time information storage unit 104. The communication control unit 114 transfers information at the time of the detection of irradiation, read out from the driving control unit 103, to the console 3.

An image processing unit 303 of the console 3 specifies, from the information at the time of the detection of irradiation, information concerning a row number corresponding to the time when reset scanning is stopped, the type of partial reset scanning when partial reset scanning is stopped (a method of selecting rows (scanning lines) which are not adjacent to each other), an output value corresponding to the time when irradiation is detected, and the like. The image processing unit 303 performs image correction so as to interpolate defects in the received captured image by using the specified information and performs image processing suitable for each type of diagnosis (TC1110 and step S1214). The display unit 4 displays the captured image for which image processing has been performed by the image processing unit 303 (TC1111 and step S1215: display of actual image).

According to each embodiment described above, it is possible to reduce a display delay concerning a preview image and display the preview image without performing correction processing for an image deterioration at the time of the detection of radiation.

The apparatus sequentially performs reset scanning on rows on the two-dimensional sensor array which are not adjacent to each other, when waiting for the start of radiation irradiation. Defects occur in only image data on rows on which partial reset scanning has been performed at the time of the detection of the start of radiation irradiation, and no defects occur in image data on rows which have not been selected for reset scanning at the time of the start of irradiation.

This makes it possible for the apparatus to generate a preview image by using only the image data obtained from rows on which no defects have occurred and to display the preview image by transferring it to the display unit without performing image deterioration correction processing for the preview image. This can reduce the delay time (display delay) until a preview image is displayed and display the preview image free from the influence of pixel value defects.

Third Embodiment

A radiation imaging apparatus according to the third embodiment of the present invention will be described next. The radiation imaging apparatus includes a radiation detection unit including a radiation detection array having a plurality of pixels configured to convert radiation into charges and arranged two-dimensionally and a plurality of scanning lines for selecting conversion elements.

A reset scanning control unit performs reset scanning control to perform reset scanning to sequentially select scanning lines which are not adjacent to each other and discharge charges accumulated in conversion elements corresponding to the scanning lines. An irradiation detection unit detects the start of radiation irradiation during reset scanning. A readout control unit stops reset scanning in accordance with the detection of the start of irradiation by the irradiation detection unit and obtain image data based on charges by reading out the charges accumulated in conversion element by radiation irradiation. A preview image generation unit 109 (generation unit) generates a preview image based on image data corresponding to scanning lines on which no reset scanning is performed during radiation irradiation. A communication control unit (output unit) outputs the preview image generated by the preview image generation unit (generation unit) to an external apparatus.

The preview image generation unit generates a preview image based on the image data obtained by removing image data corresponding to scanning lines on which reset scanning has been performed in the interval from the start of radiation irradiation to the detection of radiation irradiation from the image data read out by the readout control unit.

The reset scanning control unit and the readout control unit divide a plurality of scanning lines into a plurality of scanning line groups each including scanning lines which are not adjacent to each other, and execute scanning on one line group of the plurality of scanning line groups first and then execute scanning on the other line group.

The readout control unit reads out, in advance, charges accumulated in conversion elements on scanning lines other than the scanning line group on which reset scanning has been performed at the time of the detection of radiation irradiation. The preview image generation unit (generation unit) generates a preview image based on image data corresponding to the charges accumulated in the conversion elements on the scanning lines, which have been read out in advance.

The plurality of scanning line groups include the first line group including scanning lines arranged at even-numbered positions in the arrangement of a radiation detection array and the second line group including scanning lines arranged at odd-numbered positions. The communication control unit (output unit) includes a wireless communication circuit which wirelessly transmits the preview image generated by the preview image generation unit (generation unit). Note that a method of transmitting a preview image is not limited to wireless communication, and may be wired communication using a cable.

The radiation imaging apparatus includes a radiation detection unit having a plurality conversion elements configured to convert radiation into charges and arranged two-dimensionally. The apparatus radiation imaging apparatus includes: a reset scanning control unit configured to select scanning lines of the radiation detection unit which are not adjacent to each other and sequentially drive conversion elements on the selected scanning lines to perform reset scanning to discharge dark charges accumulated in the conversion elements; an irradiation detection unit configured to detect the start of radiation irradiation and the end of radiation irradiation; an obtaining unit configured to obtain image data by the radiation irradiation by reading out charges accumulated in the conversion elements by the radiation irradiation; a generation unit configured to generate, by using the image data, a preview image concerning a scanning line on which the reset scanning is not performed at the start of the radiation irradiation; and an output unit configured to output the preview image.

The reset scanning control unit stops the reset scanning at the start of the radiation irradiation. The obtaining unit obtains image data on a scanning line on which the reset scanning is not performed at the start of the radiation irradiation from the obtained image data by using information of said radiation detection unit at the stop of the reset scanning.

The obtaining unit obtains offset image data while the radiation is not irradiated, by reading out dark charges accumulated in the conversion elements with a lapse of time from the start of the irradiation to the end of the irradiation.

The obtaining unit obtains offset image data concerning a scanning line on which the reset scanning is not performed at the start of the radiation irradiation while the radiation is not irradiated, by reading out dark charges accumulated in the conversion elements with a lapse of time from the start of the irradiation to the end of the irradiation.

The radiation imaging apparatus includes a radiation detection unit including a radiation detection array having a plurality of conversion elements configured to convert radiation into charges and a plurality of scanning lines for selecting the conversion elements. The radiation imaging apparatus includes: a reset scanning control unit configured to perform reset scanning to discharge charges accumulated in conversion elements corresponding to the scanning lines by sequentially selecting the scanning lines which are not adjacent to each other; an irradiation detection unit configured to detect the start of radiation irradiation during reset scanning; a control unit configured to read out charges accumulated in the pixels by the radiation irradiation while stopping the reset scanning in accordance with detection of the radiation irradiation and obtain image data based on the charges; a generation unit configured to generate a preview image based on image data corresponding to a scanning line on which the reset scanning is not performed during the radiation irradiation; and an output unit configured to output the preview image to an external apparatus.

The generation unit generates, from image data read out by the readout control unit, a preview image based on image data except for image data corresponding to scanning lines on which the reset scanning has been performed in an interval from the start of the radiation irradiation to detection of the radiation irradiation.

Fourth Embodiment

The fourth embodiment will be described with reference to FIG. 13. This embodiment differs from the above embodiments in the manner of driving. The driving control entity and the target to be driven are the same as those in the above embodiments, and hence a description of them will be omitted. In this embodiment, upon entering the accumulating operation (TC1303), the apparatus performs radiation image readout operation from the row next to the row which has been scanned immediately before the accumulating operation. In the case shown in FIG. 13, the apparatus starts radiation image readout operation from a row L9 upon performing reset scanning on a row L8, and scans the (2n+1)th row and the 2 nth row.

In addition, as compared with the case shown in FIG. 11, the apparatus can reduce the accumulation time difference for each line between the 2 nth row and the (2n+1)th row, and hence can obtain an image with less noise.

Upon scanning up to the last (2n+1)th row, the apparatus returns to the initial position to scan the remaining (2n+1)th rows (up to the row number smaller by one than that corresponding to the row on which scanning is stopped). The apparatus scans L9, L11, . . . , and then scans L1, L3, L5, and L7. This completes scanning on the (2n+1)th rows. The image signal obtained by scanning on the (2n+1)th rows is transferred to an external apparatus as in the embodiment described above. Obviously, if the last row on which reset scanning has been performed before accumulating operation is the (2n+1)th row (even-numbered row), the apparatus starts radiation image readout operation from the 2 nth row.

Upon performing accumulating operation (TC1307) after the radiation image readout operation, the apparatus performs offset image readout operation in the same manner as the above radiation image readout operation. This can make the accumulation time for a radiation image closer to that for an offset image and properly correct dark components in the radiation image.

Note that if the apparatus performs scanning, of reset scanning (TC1301), on the (2n+1)th row and the 2 nth row, which has been performed immediately before accumulating operation, in midway in the interval between radiation image readout operation and accumulating operation (TC1307), the accumulation time on each row becomes closer to that for a radiation image.

Furthermore, the apparatus performs reset scanning upon reversely biasing pixels and then performs reset scanning upon forwardly biasing the pixels (refreshing operation) in the same manner between the radiation image readout operation and the accumulating operation (TC1307). This makes it possible to obtain a good offset image by recovering the dynamic range in a MIS sensor, in particular, which decreases upon X-ray detection.

In addition, the apparatus may start readout operation from, for example, the row L11 or L13 instead of the row next to the last row L8 on which reset scanning has been performed before accumulating operation. That is, it is not always necessary to start readout operation from the row next the row L8.

Fifth Embodiment

The fifth embodiment will be described with reference to FIG. 14. This embodiment differs from the above embodiments in the manner of driving. The driving control entity and the target to be driven are the same as those in the above embodiments, and hence a description of them will be omitted. In this embodiment, the apparatus simultaneously scans a plurality of rows in reset scanning. In the case shown in FIG. 14, the apparatus simultaneously turns on the TFTs connected to the row selection lines of a total of four rows, namely rows L0, L2, L4, and L6. If a driving circuit is formed from a shift register, the apparatus scans the rows L0, L2, L4, and L6 in a possible shortest time so as to simultaneously turn on the rows L0, L2, L4, and L6. In this case, although the scanning timings of the respective rows slightly shift from each other, it is possible to increase currents flowing in the bias lines substantially in the same manner as when the respective rows are turned on simultaneously in a strict sense. This contributes to an improvement in detection sensitivity. In this case, detection sensitivity is defined as, for example, the time between the instant X-ray irradiation is actually started and the instant X-ray irradiation is detected. From a different viewpoint, detection sensitivity is defined as the minimum value of the intensity of X-rays which can be detected within a predetermined time. In this case, intensity is, for example, a dose per unit time.

In addition, this embodiment provides a waiting time between scanning on the (2n+1)th row and scanning on the 2 nth row in radiation image readout operation, and transfers the image signal obtained by scanning on the (2n+1)th row to the outside. The embodiment controls this waiting time to make it come to an end when the transfer of the image signal obtained by scanning on the (2n+1)th row is complete, that is, in accordance with determination whether an ACK signal is received from the transfer destination or the timeout concerning transfer occurs. The apparatus starts scanning on the 2 nth row in accordance with such determination. Information concerning such a waiting time t_wait is stored in a memory.

Inhibiting the timing of radiation image readout operation from coinciding with that of image transfer in this manner can reduce communication noise superimposed on a readout image signal. Such driving operation produces a larger effect when performing wireless image transfer. In addition, performing image transfer in the interval between scanning on the (2n+1)th row and scanning on the 2 nth row can reduce the influence of communication noise and can eventually quicken the display of a preview image.

In addition, assume that a waiting time corresponding to t_wait stored in the memory is also provided between scanning on the (2n+1)th row and scanning on the 2 nth row in offset image readout operation. The embodiment is configured to perform control to start scanning on the 2 nth row after the elapse of t_wait since the end of scanning on the (2n+1)th row.

Note that the above embodiments may be properly combined. For example, in another embodiment, even in a case in which the apparatus starts radiation image readout operation from the row next to the last row on which reset scanning has been performed before accumulating operation as shown in FIG. 13, a waiting time is set in the interval between scanning on the (2n+1)th row and scanning on the 2 nth row in radiation image readout operation as shown in FIG. 14 to inhibit scanning, amplification of the signal obtained by scanning by an image signal amplifier, and readout operation such as A/D conversion from being performed during the transfer of the image signal obtained by scanning on the (2n+1)th row.

In another embodiment, even when simultaneously scanning a plurality of rows as shown in FIG. 14, the apparatus performs timing control so as to concurrently perform radiation image readout operation and transfer. Furthermore, the embodiments can be properly combined.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-040037, filed Feb. 28, 2013, and No. 2014-021705, filed Feb. 6, 2014, which are hereby incorporated by reference herein in their entirety.

What is claimed is:

1. A radiation imaging apparatus including a radiation detection unit including a radiation detection array having a plurality of pixels configured to detect radiation and accumulate charges and arranged two-dimensionally and a plurality of scanning lines for discharging charges accumulated in the pixels, the apparatus comprising:
   a reset control unit configured to perform reset scanning to sequentially discharge charges accumulated in the pixels;
   an irradiation detection unit configured to detect a start of radiation irradiation;
   an imaging control unit configured to perform control to stop the reset scanning in accordance with detection of the start of irradiation and obtain an image signal by reading out charges accumulated in the pixels by the radiation irradiation;
   a generation unit configured to generate image data to be used for a preview without correcting for an image signal from a pixel on which the reset scanning is performed during the radiation irradiation; and
   an output unit configured to output the image data to an external apparatus.

2. The apparatus according to claim 1, wherein the reset control unit is configured to sequentially select scanning lines which are not adjacent to each other and control reset scanning of the selected scanning lines to discharge charges accumulated in pixels connected to the selected scanning lines.

3. The apparatus according to claim 1, wherein the imaging control unit is configured to start reading out charges, from which the image signal is obtained, from a scanning line on which the reset scanning is not performed by the stop.

4. The apparatus according to claim 3, wherein the reset control unit is configured to sequentially select the scanning lines in accordance with a predetermined sequence,
   the imaging control unit is configured to read out charges from which the image signal is obtained, starting from a scanning line on which the reset scanning is not performed by the stop, in accordance with the predetermined sequence, and
   the generation unit is configured to generate image data based on image signals corresponding to a scanning line from which the readout operation has started to an N/2th scanning line from which readout operation is performed, with N representing the total number of lines from which image signals are obtained.

5. The apparatus according to claim 4, wherein the reset control unit is configured to perform the reset scanning separately on even-numbered lines and odd-numbered lines in a predetermined sequence, and
   the generation unit is configured to generate image data based on an image signal from an odd-numbered line in a case where a line being scanned when the reset scanning is stopped is an even-numbered line, and generates image data based on an image signal from an even-numbered line in a case where a line being scanned when the reset scanning is stopped is an odd-numbered line.

6. The apparatus according to claim 1, wherein the output unit is configured to output, to an external apparatus, another image data containing an image signal from a scanning line on which the reset scanning is performed during the radiation irradiation, after outputting the generated image data.

7. The apparatus according to claim 1, wherein the generation unit is configured to generate, by using the image data, a preview image concerning a scanning line on which the reset scanning is not performed at the start of the radiation irradiation.

8. The apparatus according to claim 1, wherein the reset control unit is configured to stop the reset scanning at the start of the radiation irradiation, and
   the imaging control unit is configured to obtain the image signal on a scanning line on which the reset scanning is not performed at the start of the radiation irradiation by using information of the radiation detection unit at the stop of the reset scanning.

9. The apparatus according to claim 8, wherein the imaging control unit is configured to obtain image signal on a scanning line on which the reset scanning is performed at the start of the radiation irradiation by using information of the radiation detection unit after the image signal is obtained.

10. The apparatus according to claim 1, wherein the reset control unit is configured to stop the reset scanning at the start of the radiation irradiation, and the imaging control unit is configured to obtain image signal on a scanning line on which the reset scanning is not performed at the start of the radiation irradiation from the obtained image signal by using information of the radiation detection unit at the stop of the reset scanning, and information concerning the radiation detection unit at the stop of the reset scanning includes information indicating a scanning line on which reset scanning is performed at the start of radiation irradiation and information for selecting scanning lines which are not adjacent to each other when performing reset scanning.

11. The apparatus according to claim 1, further comprising a correction unit configured to perform offset correction to remove a dark charge component of the obtained image signal obtained by the radiation irradiation; and an image processing unit configured to perform image processing for the image signal which has been subjected to the offset correction, wherein the output unit is configured to output the image signal which has been subjected to the image processing, to an external apparatus after the generated image data is output to the external apparatus by one of wireless communication and wired communication.

12. The apparatus according to claim 1, wherein the generation unit is configured to generate a reduced preview image by thinning out pixels from the obtained image signal.

13. The apparatus according to claim 1, wherein the reset control unit and the imaging control unit are configured to divide the plurality of scanning lines into a plurality of scanning line groups, each including scanning lines which are not adjacent to each other, and execute scanning on one line group of the plurality of scanning line groups and then execute scanning on the other line group, the imaging control unit is configured to read out, in advance, charges accumulated in the pixels on a scanning line other than a scanning line group on which the reset scanning is performed when irradiation of radiation is detected, and the generation unit is configured to generate a preview image based on the obtained image signal read out in advance and corresponding to charges accumulated in the pixels on the scanning line.

14. The apparatus according to claim 1, wherein the imaging control unit is configured to obtain offset data obtained on a condition that radiation is not irradiated, by reading out dark charges accumulated in the pixels with a lapse of time from the start of the irradiation to an end of the irradiation.

15. The apparatus according to claim 14, wherein after the offset data is obtained, the imaging control unit is configured to obtain offset data concerning a scanning line on which the reset scanning is performed at the start of the radiation irradiation.

16. The apparatus according to claim 1, wherein the output unit is configured to output the generated image data to an external apparatus by one of wireless communication and wired communication.

17. The apparatus according to claim 1, further comprising a display unit configured to display the outputted image data.

18. A method for radiation imaging using a radiation detection unit including a plurality of pixels arranged two-dimensionally, each configured to accumulate charges, the method comprising:

performing reset scanning to sequentially discharge charges accumulated in the pixels;
detecting a start of radiation irradiation;
stopping the reset scanning in accordance with detection of the start of irradiation;
obtaining an image signal by reading out charges accumulated in the pixels by the radiation irradiation;
generating image data to be used for a preview without correcting for an image signal from a pixel on which the reset scanning is performed during the radiation irradiation; and
outputting the image data to an external apparatus.

19. A non-transitory computer-readable storage medium storing a program for causing a computer to execute each step in a method for radiation imaging using a radiation detection unit including a plurality of pixels arranged two-dimensionally, each configured to accumulate charges, the method comprising:

performing reset scanning to sequentially discharge charges accumulated in the pixels;
detecting a start of radiation irradiation;
stopping the reset scanning in accordance with detection of the start of irradiation;
obtaining an image signal by reading out charges accumulated in the pixels by the radiation irradiation;
generating image data to be used for a preview without correcting for an image signal from a pixel on which the reset scanning is performed during the radiation irradiation; and
outputting the image data to an external apparatus.

20. A radiation imaging system comprising a radiation imaging apparatus including a radiation detection unit including a radiation detection array having a plurality of pixels configured to detect radiation and accumulate charges and arranged two-dimensionally and a plurality of scanning lines for discharging charges accumulated in the pixels and an information processing apparatus configured to process data transmitted from the radiation imaging apparatus, wherein the radiation imaging apparatus comprises
a reset control unit configured to perform reset scanning to sequentially discharge charges accumulated in the pixels;
an irradiation detection unit configured to detect a start of radiation irradiation;
an imaging control unit configured to perform control to stop the reset scanning in accordance with detection of the start of irradiation and obtain an image signal by reading out charges accumulated in the pixels by the radiation irradiation;
a generation unit configured to generate image data to be used for a preview without correcting for an image signal from a pixel on which the reset scanning is performed during the radiation irradiation; and
an output unit configured to output the image data to an external apparatus, and
the information processing apparatus comprises a display unit configured to display the outputted image data.

21. A radiation imaging system comprising:
a radiation detection unit including a radiation detection array having a plurality of pixels configured to detect radiation and accumulate charges and arranged two-dimensionally, and a plurality of scanning lines for discharging charges accumulated in the pixels;
a reset control unit configured to perform reset scanning to sequentially discharge charges accumulated in the pixels;
an irradiation detection unit configured to detect a start of radiation irradiation;
an imaging control unit configured to perform control to stop the reset scanning in accordance with detection of the start of irradiation and obtain an image signal by reading out charges accumulated in the pixels by the radiation irradiation; and a generation unit configured to generate image data to be used for a preview without correcting for an image signal from a pixel on which the reset scanning is performed during the radiation irradiation, and generate image data to be used for an actual image by correcting an image signal from a pixel on which the reset scanning is performed during the radiation irradiation.

22. The system according to claim 21, wherein the reset control unit is configured to sequentially select scanning lines which are not adjacent to each other and control reset scanning of the selected scanning lines to discharge charges accumulated in pixels connected to the selected scanning lines.

23. The system according to claim 21, wherein the reset control unit is configured to perform the reset scanning separately on even-numbered lines and odd-numbered lines in a predetermined sequence, and the generation unit is configured to generate image data to be used for the preview based on an image signal from an odd-numbered line in a case where a line being scanned when the reset scanning is stopped is an even-numbered line, and generates image data to be used for the preview based on an image signal from an even-numbered line in a case where a line being scanned when the reset scanning is stopped is an odd-numbered line.

24. The system according to claim 21, further comprising a display unit configured to display a preview image based on the generated image data to be used for the preview and an actual image based on the generated image data to be used for the actual image.

25. A radiation imaging system comprising:

a radiation detection unit configured to have a radiation detection array having a plurality of pixels configured to detect radiation and accumulate charges and arranged two-dimensionally, and a plurality of scanning lines for discharging charges accumulated in the pixels;

a reset control unit configured to perform reset scanning to sequentially discharge charges accumulated in the pixels;

an irradiation detection unit configured to detect a start of radiation irradiation;

an imaging control unit configured to perform control to stop the reset scanning in accordance with detection of the start of irradiation and obtain an image signal by reading out charges accumulated in the pixels by the radiation irradiation, wherein the reset control unit and the imaging control unit divide the plurality of scanning lines into a plurality of scanning line groups, each including scanning lines which are not adjacent to each other, and execute scanning on one line group of the plurality of scanning line groups and then execute scanning on the other line group; and a generation unit configured to generate, among the plurality of scanning line groups, image data except an image signal of a scanning line group on which the reset scanning is performed during the radiation irradiation.

26. The system according to claim 25, wherein the plurality of scanning line groups are set based on even-numbered lines or odd-numbered lines, and the generation unit is configured to generate image data based on an image signal from an odd-numbered line in a case where a line being scanned when the reset scanning is stopped is an even-numbered line, and generates image data based on an image signal from an even-numbered line in a case where a line being scanned when the reset scanning is stopped is an odd-numbered line.

27. The system according to claim 25, further comprising a display unit configured to display an image based on the generated image data.

* * * * *